United States Patent
Chun et al.

(10) Patent No.: US 11,188,877 B2
(45) Date of Patent: Nov. 30, 2021

(54) METHOD FOR PROVIDING MEDICAL SERVICE AND ELECTRONIC DEVICE SUPPORTING THE SAME

(71) Applicant: Samsung Electronics Co., Ltd, Gyeonggi-do (KR)

(72) Inventors: Jae Woong Chun, Gyeonggi-do (KR); Kyung Hee Lee, Gyeonggi-do (KR); Hae Dong Lee, Daegu (KR); Won Suk Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1155 days.

(21) Appl. No.: 15/402,115

(22) Filed: Jan. 9, 2017

(65) Prior Publication Data

US 2017/0199974 A1    Jul. 13, 2017

(30) Foreign Application Priority Data

Jan. 8, 2016 (KR) .................. 10-2016-0002830

(51) Int. Cl.
*G06Q 10/10* (2012.01)
*G16H 40/67* (2018.01)
*G06Q 40/08* (2012.01)

(52) U.S. Cl.
CPC .......... *G06Q 10/109* (2013.01); *G06Q 40/08* (2013.01); *G16H 40/67* (2018.01)

(58) Field of Classification Search
CPC .. G06F 19/3418; G06F 19/328; G06F 19/321; G06Q 10/109; F21V 7/22; F21V 7/00; C25D 17/008; C25D 17/10; C25D 17/007; C25D 17/005; C25D 17/06
See application file for complete search history.

(56) References Cited

U.S. PATENT DOCUMENTS

| 8,635,084 B2 | 1/2014 | Phillips | |
| 2012/0166221 A1* | 6/2012 | Phillips | G06F 19/3418 705/3 |
| 2014/0108055 A1 | 4/2014 | Phillips | |
| 2014/0195255 A1* | 7/2014 | Ghosh | G06F 19/3418 705/2 |
| 2015/0213217 A1* | 7/2015 | Amarasingham | G16H 50/30 705/2 |
| 2017/0228515 A1* | 8/2017 | Schoenberg | G06Q 10/06375 |

FOREIGN PATENT DOCUMENTS

WO    WO-2008103811 A2 *    8/2008    ............. G16H 10/60

OTHER PUBLICATIONS

Devaraj, Current Trends And Future Challenges In Wireless Telemedicine System, 3rd International Conference on Electronics Computer Technology (vol. 4, pp. 417-421) (Year: 2011).*

* cited by examiner

*Primary Examiner* — Rachelle L Reichert

(57) ABSTRACT

An electronic device includes a memory that stores one or more medical policies and a processor. The processor is configured to obtain a request for execution of an application that provides a medical service, to decide a medical policy, which corresponds to a location of the electronic device, from among the one or more medical policies, and to selectively provide at least one function of the application based on a medical service performing method, which is determined based at least on the medical policy, from among one or more medical service performing methods.

9 Claims, 13 Drawing Sheets

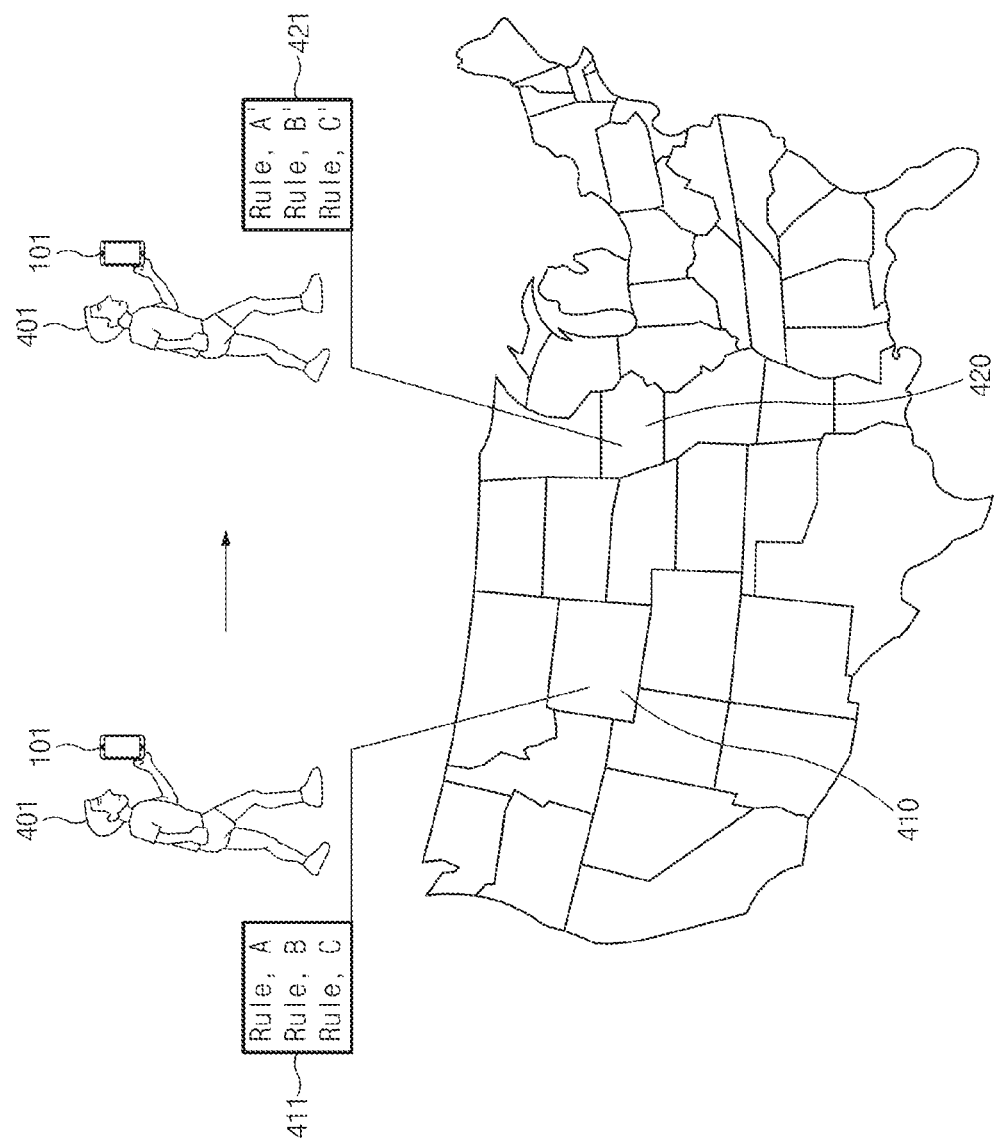

| State | Physical exam | Pre-relationship | Informed consent | Telepresenter | ... | consultation by out of state physicians |
|---|---|---|---|---|---|---|
| Alabama | ✓ | ✓ | | | | ✓ |
| Alaska | ✓ | ✓ | ✓ | ✓ | | ✓ |
| Arizona | ✓ | ✓ | | ✓ | | ✓ |
| : | | | | | | |
| : | | | | | | |
| Wisconsin | | | | | | ✓ |
| Wyoming | | | | | | ✓ |

FIG. 5

METHOD FOR PROVIDING MEDICAL SERVICE AND ELECTRONIC DEVICE SUPPORTING THE SAME

CROSS-REFERENCE TO RELATED APPLICATION AND CLAIM OF PRIORITY

The present application is related to and claims the benefit under 35 U.S.C. § 119(a) of a Korean patent application filed on Jan. 8, 2016 in the Korean Intellectual Property Office and assigned Serial number 10-2016-0002830, the entire disclosure of which is hereby incorporated by reference.

TECHNICAL FIELD

The present disclosure relates to a method, which is capable of providing a medical service, and an electronic device supporting the same.

BACKGROUND

A medical service that is provided to a patient by using an electronic device may be provided in various manners. Nowadays, with the development of technologies, a telemedicine service that allows a doctor (or a hospital) to examine a patient far away from the doctor by using a communication technology is being used as one medical service manner. The telemedicine service means that a medical service provider (e.g., a hospital or a doctor) and a medical service recipient (e.g., a patient) who are geographically separated from each other provide services, for example, medical diagnosis, treatment, and the like, by using information and communication technologies. The telemedicine service may be gradually expanded due to development of a smartphone or a wearable device (e.g., a smart watch, a smart band, or the like), expansion of a communication-capable Internet of things (IoT) medical device, and development of information and communication technologies.

In the process of providing the telemedicine service, there are various regulations that include requirements, with which a telemedicine service provider complies, to comply with provisions: to protect privacy of a patient, to protect patient information, and to protect the right of a patient receiving the telemedicine service. A typical one among the regulations includes Healthcare Insurance Portability and Accountability Act (HIPAA), Health Level Seven (HL7), or the like. These regulations provide provisions associated with compatibility, security, privacy, and the like for a health service user and a health service provider. HIPAA also includes mandatory measures in the case where the regulations are violated.

In the United States, telemedicine service policies of respective states may be different from each other, and the technical part for complying with the regulations need to be premised to provide the telemedicine service.

In the case where medical service policies or medical service regulations vary with areas, the varied policies or regulations are not effectively applied to a conventional electronic device that provides the telemedicine service. Accordingly, the conventional electronic device fails to provide the telemedicine service based on a policy of each area.

SUMMARY

To address the above-discussed deficiencies, it is a primary object to provide an electronic device includes a memory that stores one or more medical policies and a processor. The processor is configured to obtain a request for execution of an application that provides a medical service, to decide a medical policy, which corresponds to a location of the electronic device, from among the one or more medical policies, and to selectively provide at least one function of the application based on a medical service performing method, which is determined based at least on the medical policy, from among one or more medical service performing methods.

Other aspects, advantages, and salient features of the disclosure will become apparent to those skilled in the art from the following detailed description, which, taken in conjunction with the annexed drawings, discloses various embodiments of the present disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 4 is a drawing illustrating a change in a medical service policy based on movement of a user, according to various embodiments;

FIG. 5 illustrates a table for a medical policy changed according to an area, according to various embodiments;

Throughout the drawings, it should be noted that like reference numbers are used to depict the same or similar elements, features, and structures.

DETAILED DESCRIPTION

Figure 1:
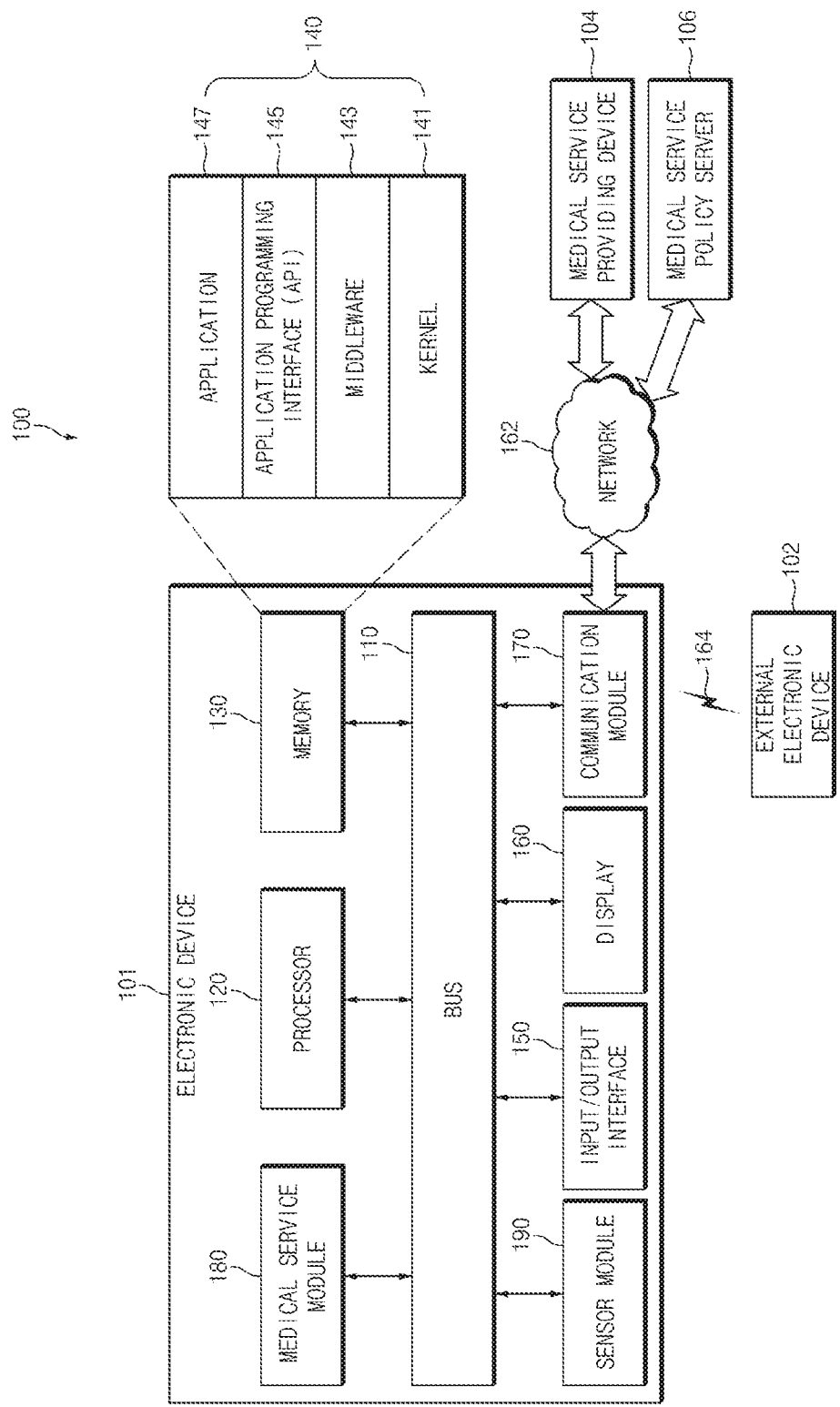
FIG. 1 illustrates an electronic device in a network environment according to various embodiments.

FIGS. 1 through 12, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged services and electronical devices.

Hereinafter, various embodiments of the present disclosure will be described with reference to the accompanying drawings. Accordingly, those of ordinary skill in the art will recognize that modification, equivalent, and/or alternative on the various embodiments described herein can be variously made without departing from the scope and spirit of the present disclosure. With regard to description of drawings, similar components may be marked by similar reference numerals.

In the disclosure disclosed herein, the expressions "have", "may have", "include" and "comprise", or "may include" and "may comprise" used herein indicate existence of corresponding features (for example, elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used herein may refer to various elements of various embodiments of the present disclosure, but do not limit the elements. For example, such terms are used only to distinguish an element from another element and do not limit the order and/or priority of the elements. For example, a first user device and a second user device may represent different user devices irrespective of sequence or importance. For example, without departing the scope of the present disclosure, a first element may be referred to as a second element, and similarly, a second element may be referred to as a first element.

It will be understood that when an element (for example, a first element) is referred to as being "(operatively or communicatively) coupled with/to" or "connected to" another element (for example, a second element), it can be directly coupled with/to or connected to the other element or an intervening element (for example, a third element) may be present. In contrast, when an element (for example, a first element) is referred to as being "directly coupled with/to" or "directly connected to" another element (for example, a second element), it should be understood that there are no intervening element (for example, a third element).

According to the situation, the expression "configured to" used herein may be used as, for example, the expression "suitable for", "having the capacity to", "designed to", "adapted to", "made to", or "capable of". The term "configured to (or set to)" must not mean only "specifically designed to" in hardware. Instead, the expression "a device configured to" may mean that the device is "capable of" operating together with another device or other components. CPU, for example, a "processor configured to (or set to) perform A, B, and C" may mean a dedicated processor (for example, an embedded processor) for performing a corresponding operation or a generic-purpose processor (for example, a central processing unit (CPU) or an application processor) which may perform corresponding operations by executing one or more software programs which are stored in a memory device.

Terms used in this specification are used to describe specified embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude embodiments of the present disclosure.

An electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), MP3 players, mobile medical devices, cameras, and wearable devices. According to various embodiments of the present disclosure, the wearable devices may include accessories (for example, watches, rings, bracelets, ankle bracelets, glasses, contact lenses, or head-mounted devices (HMDs)), cloth-integrated types (for example, electronic clothes), body-attached types (for example, skin pads or tattoos), or implantable types (for example, implantable circuits).

In some embodiments of the present disclosure, the electronic device may be one of home appliances. The home appliances may include, for example, at least one of a digital video disk (DVD) player, an audio, a refrigerator, an air conditioner, a cleaner, an oven, a microwave oven, a washing machine, an air cleaner, a set-top box, a home automation control panel, a security control panel, a TV box (for example, Samsung HomeSync™, Apple TV™, or Google TV™), a game console (for example, Xbox™ or PlayStation™), an electronic dictionary, an electronic key, a camcorder, or an electronic panel.

In another embodiment of the present disclosure, the electronic device may include at least one of various medical devices (for example, various portable medical measurement devices (a blood glucose meter, a heart rate measuring device, a blood pressure measuring device, and a body temperature measuring device), a magnetic resonance angiography (MRA), a magnetic resonance imaging (MRI) device, a computed tomography (CT) device, a photographing device, and an ultrasonic device), a navigation system, a global navigation satellite system (GNSS), an event data recorder (EDR), a flight data recorder (FDR), a vehicular infotainment device, electronic devices for vessels (for example, a navigation device for vessels and a gyro compass), avionics, a security device, a vehicular head unit, an industrial or home robot, an automatic teller's machine (ATM) of a financial company, a point of sales (POS) of a store, or an internet of things (for example, a bulb, various sensors, an electricity or gas meter, a spring cooler device, a fire alarm device, a thermostat, an electric pole, a toaster, a sporting apparatus, a hot water tank, a heater, and a boiler).

According to some embodiments of the present disclosure, the electronic device may include at least one of a furniture or a part of a building/structure, an electronic board, an electronic signature receiving device, a projector, or various measurement devices (for example, a water service, electricity, gas, or electric wave measuring device). In various embodiments of the present disclosure, the electronic device may be one or a combination of the aforementioned devices. The electronic device according to some embodiments of the present disclosure may be a flexible electronic device. Further, the electronic device according to an embodiment of the present disclosure is not limited to the aforementioned devices, but may include new electronic devices produced due to the development of technologies.

Hereinafter, electronic devices according to an embodiment of the present disclosure will be described with reference to the accompanying drawings. The term "user" used herein may refer to a person who uses an electronic device or may refer to a device (for example, an artificial electronic device) that uses an electronic device.

FIG. 1 illustrates an electronic device 101 in a network environment 100, according to various embodiments.

Referring to FIG. 1, in various embodiments, the electronic device 101 may be a device that performs a medical service. For example, a user may perform an application that is installed in the electronic device 101 and that provides the medical service. The electronic device 101 may perform a user interface (UI) or a user experience (UX) for providing the medical service and may be connected with an electronic device of a hospital or a doctor that provides a telemedicine service. The user can talk to a doctor about a disease and can receive a prescription based on a symptom, through a video call or the like.

According to various embodiments, the electronic device 101 can be connected with an external device (e.g., an external electronic device 102, a medical service providing device 104, or a medical service policy server 106) through a network 162 or a local-area communication 164. The electronic device 101 can include a bus 110, a processor 120, a memory 130, an input/output (I/O) interface 150, a display 160, and a communication module 170. According to an embodiment, the electronic device 101 may not include at least one of the above-described elements or can further include other element(s).

For example, the bus 110 can interconnect the above-described elements 120 to 170 and can include a circuit for conveying communications (e.g., a control message and/or data) among the above-described elements.

The processor 120 (e.g., the processor 110 of FIG. 1) can include one or more of a central processing unit (CPU), an application processor (AP), or a communication processor (CP). The processor 120 can perform, for example, data processing or an operation associated with control and/or communication of at least one other element(s) of the electronic device 101.

The memory 130 (e.g., the memory 160 of FIG. 1) can include a volatile and/or nonvolatile memory. For example, the memory 130 can store instructions or data associated with at least one other element(s) of the electronic device 101. According to an embodiment, the memory 130 can store software and/or a program 140. The program 140 can include, for example, a kernel 141, a middleware 143, an application programming interface (API) 145, and/or an application program (or "application") 147. At least a part of the kernel 141, the middleware 143, or the API 145 can be called an "operating system (OS)".

The kernel 141 can control or manage system resources (e.g., the bus 110, the processor 120, the memory 130, and the like) that are used to execute operations or functions of other programs (e.g., the middleware 143, the API 145, and the application program 147). Furthermore, the kernel 141 can provide an interface that allows the middleware 143, the API 145, or the application program 147 to access discrete elements of the electronic device 101 so as to control or manage system resources.

The middleware 143 can perform a mediation role such that the API 145 or the application program 147 communicates with the kernel 141 to exchange data.

Furthermore, the middleware 143 can process one or more task requests received from the application program 147 according to a priority. For example, the middleware 143 can assign the priority, which makes it possible to use a system resource (e.g., the bus 110, the processor 120, the memory 130, or the like) of the electronic device 101, to at least one of the application program 147. For example, the middleware 143 can process the one or more task requests according to the priority assigned to the at least one, which makes it possible to perform scheduling or load balancing on the one or more task requests.

The API 145 can be an interface through which the application 147 controls a function provided by the kernel 141 or the middleware 143, and can include, for example, at least one interface or function (e.g., an instruction) for a file control, a window control, image processing, a character control, or the like.

According to various embodiments, the memory 130 can store data for providing the medical service. According to various embodiments, the data can be medical information data associated with the user or measurement data associated with the user.

According to various embodiments, the memory 130 can store information about a telemedicine policy in an area in which the electronic device 101 (or the user) is situated. Alternatively, the memory 130 can store information about the telemedicine policy in an area to which the electronic device 101 (or the user) is scheduled to move. The telemedicine policy can be information about a premise for performing a telemedicine service.

According to various embodiments, the memory 130 can store the telemedicine policy in the form of a table or a database for each nation or for each administrative district (e.g., a state) of a specific nation. According to various embodiments, the processor 120 can receive a medical service policy from the external device (e.g., the medical service policy server 106) and can store the medical service policy. In the case where the medical service policy in an area in which the user is situated or to which the user is scheduled to move is not in the memory 130, the electronic device 101 can request the medical service policy in the area from the external device and can store the medical service policy in the area.

According to various embodiments, the memory 130 can store schedule information (e.g., an airline ticket information, hotel reservation information, schedule information stored in a schedule app, or the like) of the user. The stored schedule information can be used in the case where the user performs the medical service in an area to which the user moves.

The I/O interface 150 can transmit an instruction or data, input from a user or another external device, to other element(s) of the electronic device 101. Furthermore, the I/O interface 150 can output an instruction or data, received from other component(s) of the electronic device 101, to a user or another external device.

The display 160 can include, for example, a liquid crystal display (LCD), a light-emitting diode (LED) display, an organic LED (OLED) display, or a microelectromechanical systems (MEMS) display, or an electronic paper display. The display 160 can display, for example, various kinds of content (e.g., a text, an image, a video, an icon, a symbol, and the like) to a user. The display 160 can include a touch screen and can receive, for example, a touch, gesture, proximity, or hovering input using an electronic pen or a portion of a user's body.

According to various embodiments, the display 160 can output an execution screen of an application for a telemedicine service. For example, the user can select one from a list of hospitals or a list of doctors displayed through the display 160 and can be consulted about a disease from the selected doctor through a video call.

The communication module 170 can establish communication between, for example, the electronic device 101 and the external device (e.g., the external electronic device 102, the medical service providing device 104, or the medical service policy server 106). For example, the communication module 170 can be connected to the network 162 through wireless communication or wired communication to communicate with the external device (e.g., the medical service providing device 104 or the medical service policy server 106).

According to various embodiments, the communication module 170 can support a satellite navigation system, such as a global positioning system (GPS), a global navigation satellite system (Glonass), a European global satellite-based navigation system (Galileo), or the like, an inertial navigation system that uses an angular-speedometer/accelerometer, long distance communication, such as 2G, 3G, 4G, 5G, or the like, and short distance communication such as wireless fidelity (Wi-Fi), Bluetooth (BT), Bluetooth low energy (BLE), or the like, which decides a location of the user.

According to various embodiments, the communication module 170 can recognize the location of the user by using an inertial sensor such as an angular-velocity or acceleration sensor through a method such as dead reckoning or the like. The method can be used in a radio shadow area, such as indoor space, of a satellite navigation system.

According to various embodiments, the communication module 170 can perform data communication for the medical service. For example, the communication module 170 can receive information about the medical service policy in a specific area from the medical service policy server 106. In addition, the communication module 170 can send body measurement information of the user to the medical service providing device 104 and can receive the result of the medical service from the medical service providing device 104.

The wireless communication can include at least one of, for example, LTE (long-term evolution), LTE-A® (LTE Advance), CDMA (Code Division Multiple Access), WCDMA® (Wideband CDMA), UMTS® (Universal Mobile Telecommunications System), WiBro® (Wireless Broadband), or GSM® (Global System for Mobile Communications), or the like, as cellular communication protocol. Furthermore, the wireless communication can include, for example, a local area network 164. The local area network 164 can include at least one of a wireless fidelity® (Wi-Fi®), a near field communication (NFC), MST(magnetic stripe transmission), or a global navigation satellite system (GNSS), or the like.

The MST can generate a pulse in response to transmission data using an electromagnetic signal, and the pulse can generate a magnetic field signal. The electronic device 101 can transfer the magnetic field signal to point of sales (POS), and the POS can detect the magnetic field signal using a MST reader. The POS can recover the data by converting the detected magnetic field signal to an electrical signal.

The GNSS can include at least one of a global positioning system (GPS), a global navigation satellite system (Glonass), Beidou Navigation Satellite System (hereinafter referred to as "Beidou"), the European global satellite-based navigation system (Galileo), or the like. In this specification, "GPS" and "GNSS" can be interchangeably used.

The wired communication can include at least one of, for example, a universal serial bus (USB), a high definition multimedia interface (HDMI), a recommended standard-232 (RS-232), a plain old telephone service (POTS), or the like. The network 162 can include at least one of telecommunications networks, for example, a computer network (e.g., LAN or WAN), an Internet, or a telephone network.

A medical service module 180 can collect information for providing the medical service and can decide the medical service policy associated with the information. The medical service module 180 can drive an application that provides the medical service. Additional information about a configuration or a function of the medical service module 180 can be provided with reference to FIG. 2. In FIG. 1, it is illustrated that the medical service module 180 and the processor 120 are separated. However, embodiments are not limited thereto. For example, the medical service module 180 can be included as a part of the processor 120.

A sensor module 190 can include various sensors that collect biometric information of the user. For example, the sensor module 190 can include a pedometer, a sphygmomanometer, a blood glucose meter, a photoplethysmography (PPG) sensor, an electrocardiogram (ECG) sensor, an electromyography sensor (EMG) sensor, an electroencephalogram (EEG) sensor, an oxygen saturation measuring sensor, a skin moisture measuring sensor, an obesity meter, a body temperature sensor, and the like.

According to various embodiments, the sensor module 190 can include a fingerprint sensor, an iris recognition sensor, a face recognition reader, a hand geometry reader, a hand vein reader, a speech recognition reader, a handwriting signature recognizer for recognizing a biometric feature of the user and can further include a camera, an IR camera, a touch sensor, a microphone, and the like.

The sensor module 190 can include a health sensor that collects one or more biometric signals from the user. The health sensor can collect raw data for measuring one or more of a blood pressure, a blood flow, a heart rate (e.g., HRM or HRV), a body temperature, a respiratory rate, an oxygen saturation, a cardio tone, a blood glucose, a waist circumference, a height, a weight, a body fat, a calorie consumption, an EEG, a voice, a skin resistance, an EMG, an ECG, a gait, an ultrasound image, a sleep state, the look of a face (e.g., a face), dilated pupils, and eye blinking of the user.

According to various embodiments, the processor 120 can extract information about a biometric feature by analyzing the biometric signals collected through the sensor module 190. By way of example, the processor 120 can collect a pulse wave signal through a heart rate variability (HRV) sensor. The processor 120 can obtain primary biometric feature information such as an average heart rate, a heartbeat distribution, and the like by analyzing of the pulse wave signal, and can obtain secondary biometric feature information such as a stress state and a vascular aging, which is high-level information, by processing of the biometric feature information.

According to various embodiments, a health sensor can simply output a collected user biometric signal or can output biometric feature information obtained by analyzing the biometric signal through an embedded processor.

According to various embodiments, the processor 120 can collect information sensed by the external device (e.g., the external electronic device 102). For example, the processor 120 can collect, through the communication module 170, biometric information measured through a smart band, in which the ECG sensor is embedded, or a smart watch in which the PPG sensor is embedded. As another example, the processor 120 can receive a biometric signal, which the HRV sensor which is included in an ear clip collects, and can extract biometric feature information based on the biometric signal. The extracted biometric feature information can be sent to a device, which extracts the biometric feature information, or one or more other devices. For example, if the electronic device 101 being a smartphone has extracted the biometric feature information, the electronic device 101 can output the information in a display of a smart watch or can output the information through a speaker of the ear clip in the form of a voice.

According to various embodiments, the sensor module 190 can include a touch sensor, a key input sensor, an impact sensor, a vibration sensor, and the like.

According to various embodiments, one sensor included in the sensor module 190 can sense two or more pieces of information. For example, the acceleration sensor can measure the motion of the user and the number of steps at the same time. As another example, the PPG sensor can be used as a sensor of biometric information such as a heart rate and a stress and can be used as a proximity sensor based on an amount of light thus received. As another example, the ECG sensor can detect an emotional recognition, a heart rate, and a heart rate variation (HRV) based on the ECG Analysis of a user and can be used as an authentication for distinguishing the user.

According to various embodiments, a sensor included in the sensor module 190 can be driven at all times with an electronic device powered on. As another example, the sensor can be driven according to an input (e.g., a key input, a button input, a GUI input, or gesture recognition) of the user. As another example, if one sensor is operated, a sensor associated with the operation of the one sensor can be automatically driven.

According to various embodiments, a sensor included in the sensor module 190 can be embedded in the electronic device 101, can be embedded in another electronic device, or can be a sensor mounted in an external environment (e.g., indoor space, outdoor space, a building, a base station, or the like).

The medical service providing device 104 can be a device of a service provider that provides the medical service. For example, the medical service providing device 104 can be a dedicated terminal, which a hospital operates, for the medical service. As another example, the medical service providing device 104 can be a personal terminal (e.g., a desktop personal computer (PC), a smartphone, a tablet PC, or the like) of a doctor that is in charge with the medical service.

According to various embodiments, the medical service providing device 104 can provide a service such as diagnosis of health condition of the user, prescription, lifestyle guide, or the like by using biometric information of the user received from the electronic device 101.

According to various embodiments, the medical service providing device 104 can comply with a regulation such as HIPAA, Food and Drug Administration (FDA), a regulation in an area in which a telemedicine service provider is situated, or the like to provide the medical service. The medical service providing device 104 can be situated in an area in which the same regulation as that of the user is applied to the medical service or can be situated in an area in which a regulation different from that of the user is applied to the medical service.

The medical service policy server 106 can store the medical service policy (or a regulation of the medical service) that is a prerequisite for performing the medical service. The medical service policy server 106 can store medical service policies that are different from each other for administrative districts (e.g., states) in one nation. As another example, the medical service policy server 106 can store medical service policies that are different from each other for nations. The medical service policy server 106 can provide the latest medical service policy information in response to a request of the electronic device 101. Hereinafter, it is described that the medical service policy varies for each area in one nation. However, embodiments are not limited thereto. For example, embodiments can be applied to the case where the medical service policies are different between different nations.

Figure 2:
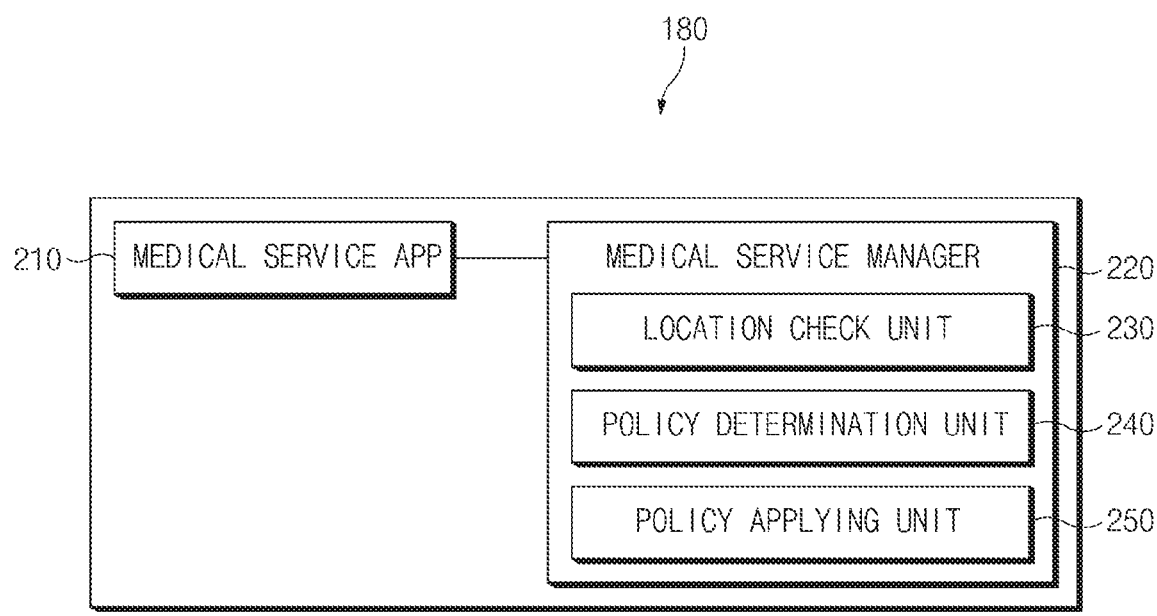
FIG. 2 illustrates a configuration of a medical service module, according to various embodiments.

FIG. 2 illustrates a configuration of a medical service module, according to various embodiments.

Referring to FIG. 2, the medical service module 180 can include a medical service app 210 and a medical service manager 220 that drives the medical service app 210.

The medical service app 210 can be an application that provides a medical service (e.g., a telemedicine service) to a user. The medical service app 210 can perform a UI or a UX for providing the medical service. The user can decide information provided through the medical service app 210 and can select or perform a necessary item. For example, the user can select one from a list of hospitals or a list of doctors that is displayed through the medical service app 210 and can be consulted about a disease from the selected doctor through a video call. As another example, the user can decide a medical service policy applied at a location, at which the user is currently situated, or the changed medical service policy in another area (e.g., an area in which the user has received the medical service before), through the medical service app 210. In addition, the user can decide an item that is needed to perform the medical service at a current location. An exemplary execution screen of the medical service app 210 can be provided through a separate drawing.

The medical service manager 220 can collect and process information that is needed to drive the medical service app 210. According to various embodiments, the medical service manager 220 can decide the medical service policy for using the medical service based on information about a location in which the user is currently situated. The medical service manager 220 can decide a difference between a medical service policy in an area (hereinafter called "first area"), in which the user has used the medical service before, and a medical service policy in an area (hereinafter called "second area") in which the user wants to perform a current medical service. The medical service manager 220 can notify the user of necessary information or can perform a necessary prework based on the changed medical service policy.

According to various embodiments, the medical service manager 220 can include a location check unit 230, a policy determination unit 240, and a policy applying unit 250. The location check unit 230, the policy determination unit 240, and the policy applying unit 250 can be classified according to their functions. Some of the location check unit 230, the policy determination unit 240, and the policy applying unit 250 can be integrated or separated.

The location check unit 230 can decide the current location of the user, which wants to use the medical service, or a location corresponding to a specified schedule by using the communication module 170, the sensor module 190, or the like. According to various embodiments, the location check unit 230 can decide a location by using the communication module 170, the sensor module 190, or content (e.g., content extracted from an airline ticket, a theater ticket, a hotel reservation confirmation letter, or the like or information extracted from a schedule app) that is extracted from a text or an image. According to various embodiments, the location check unit 230 can decide location information of the user (or the electronic device 101 that the corresponding user is using), which wants to use the medical service, by using at least one or more of a location sensor, network information, an application. The location information can include at least one or more of local information such as a nation, an administrative district, a road name or absolute location information (e.g., latitude/longitude).

For example, to determine a location, the location check unit 230 can use Internet protocol (IP) address information used to connect to a network such as an Internet. As another example, the location check unit 230 can collect location information of the user through another application that is executed by the electronic device 101. The location check unit 230 can collect information about current location of the user or a location to which the user will move in the future by using place information recorded in a scheduler app, a mobile coupon, payment information, a mobile ticket (e.g., an airline ticket, a theater ticket, or the like), or the like.

The policy determination unit 240 can search for the medical service policy, which is capable of being used in a corresponding location, based on the location information generated by the location check unit 230. The medical service policy can include at least one or more of general-purposed information and information applied in a specific area.

According to various embodiments, the policy determination unit 240 can request a medical service policy from an external device (e.g., the medical service policy server 106) based on the location information. In the case where the policy determination unit 240 receives the medical service policy in a corresponding area from the external device, the policy determination unit 240 can store the medical service policy in the memory 130.

The policy applying unit 250 can determine a condition for performing the medical service in an area in which the user is currently situated. The policy applying unit 250 can generate the condition that includes at least one or more of a service range of a medical service in an area in which the user is situated, an element which is necessary to provide a service, a privacy rule, a range in which a security is applied, a step rule in which a telemedicine service is performed, restriction or cancellation of a related function, generation or cancellation of a step rule for complying with a law or a regulation of a corresponding area, suggestion, generation, or cancellation of necessary data, recommendation or activation of an appropriate means for performing a medical service, and a rule for performing a function of operating in conjunction with another application program.

According to various embodiments, additionally, the policy applying unit 250 can extract the difference between a regulation found at a previous location and a regulation found at the changed location and can generate a rule on the changed part by using the extracted difference.

According to various embodiments, an electronic device includes a memory configured to store one or more medical policies and a processor, wherein the processor is configured to obtain a request for execution of an application that provides a medical service, decide a medical policy, which corresponds to a location of the electronic device, from among the one or more medical policies and selectively provide at least one function of the application based on a medical service performing method, which is determined based at least on the medical policy, from among one or more medical service performing methods.

According to various embodiments, the electronic device further includes a communication module or a sensor module configured to obtain information corresponding to the location.

According to various embodiments, the processor is configured to determine a location of the electronic device by extracting a location to which a user is scheduled to move.

According to various embodiments, the processor is configured to select a telemedicine policy of the one or more medical policies as at least a part of the medical policy.

According to various embodiments, the determined medical service performing method comprises an authentication procedure, an authentication method, whether to check an item in a consent form, a medical service method, or a combination thereof.

According to various embodiments, the electronic device further includes a communication module, wherein the processor is configured to receive at least some of the one or more medical policies from an external electronic device by using the communication module.

According to various embodiments, the processor is configured to perform the at least one function if the medical policy satisfies a first condition and refrain from performing the at least one function if the medical policy satisfies a second condition.

According to various embodiments, the processor is configured to perform the at least one function in a first mode if the medical policy satisfies a first condition and perform the at least one function in a second mode if the medical policy satisfies a second condition.

According to various embodiments, the processor is configured to perform a first set of functions among functions of the application as the at least one function if the medical policy satisfies a first condition and perform a second set of functions among the functions as the at least one function if the medical policy satisfies a second condition.

According to various embodiments, the application includes a first application and a second application, and the processor is configured to perform a function of the first application as the at least one function if the medical policy satisfies a first condition and perform a function of the second application as the at least one function if the medical policy satisfies a second condition.

According to various embodiments, the processor is configured to receive information about the location from an application.

According to various embodiments, the processor is configured to extract information about the location from an image stored in the memory.

Figure 3A:
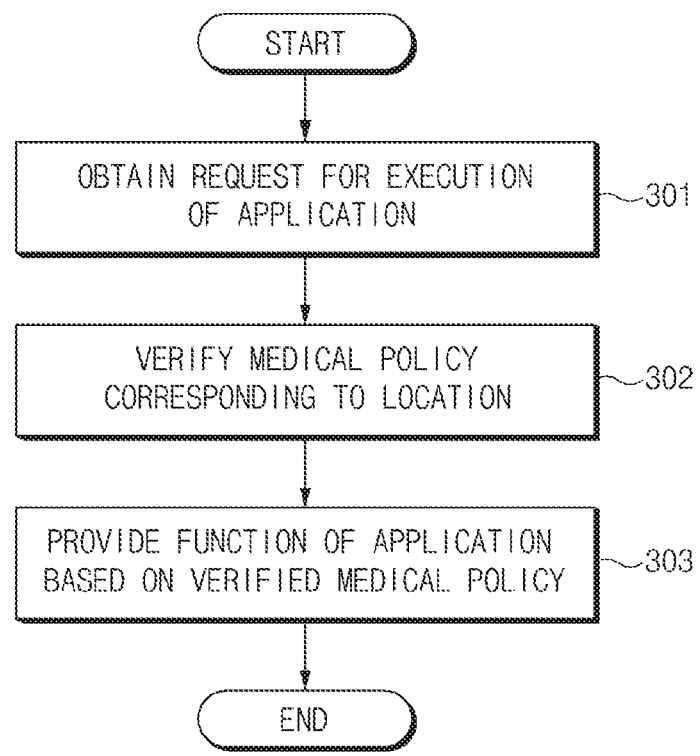
FIGS. 3A and 3B are flowcharts for describing a method for providing a medical service, according to various embodiments.

FIG. 3A is a flowchart for describing a method for providing a medical service, according to various embodiments.

Referring to FIG. 3A, in operation 301, the processor 120 (e.g., the medical service module 180) can obtain a request for execution of an application that provides the medical service. For example, a user can start the medical service app 210 by using a smartphone or a tablet PC to receive the medical service. The processor 120 can receive a signal associated with the execution of the application from the medical service app 210.

In operation 302, the processor 120 can decide a medical policy, which corresponds to a location of the electronic device 101, from among one or more medical policies. According to various embodiments, the processor 120 can select a telemedicine policy of the one or more medical policies as at least a part of the medical policy.

For example, in a first location, a preliminary interview with a doctor is not required to perform a telemedicine service. However, in the case where the preliminary interview with a doctor is not required in a second location, the processor 120 can decide a medical policy in each location.

According to various embodiments, the processor 120 can collect location information (current location information of the user or information about a location to which the user is scheduled to move) of the electronic device 101 by using the communication module 170, the sensor module 190, or content (e.g., information extracted from an airline ticket, a theater ticket, a hotel reservation confirmation letter, or the like). According to various embodiments, the processor 120 can extract a location, to which a user is scheduled to move, based at least on schedule information stored in the memory 130.

According to various embodiments, the medical policy (e.g., medical service policy) can be stored in the memory 130 of the electronic device 101 or can be received from an external device.

In operation 303, the processor 120 can selectively provide at least one function of the application based on a medical service performing method, which is determined based at least on the decided medical policy, from among one or more medical service performing methods. According to various embodiments, the medical service performing method can include an authentication procedure, an authentication method, whether to check an item in a consent form, a medical service method, or a combination thereof.

For example, in the case where the decided medical policy permits a medical service using a first function (e.g., a video call) and does not permit a medical service using a second function (e.g., a voice call), the processor 120 can activate the first function and can restrict the second function.

As another example, in the case where the decided medical policy requires the informed consent of the user, the processor 120 can output a screen for agreeing to the medical service or can output a screen for describing a method for performing an informed consent process. The user can decide an output screen and can agree to a medical service. In the case where the informed consent process is completed, the processor 120 can perform the medical service in the second location.

According to various embodiments, in the case where the medical policy satisfies a first condition, the processor 120 can perform the at least one function. In the case where the medical policy satisfies a second condition, the processor 120 can refrain from performing the at least one function.

According to various embodiments, in the case where the medical policy satisfies the first condition, the processor 120 can perform the at least one function in a first mode. In the case where the medical policy satisfies the second condition, the processor 120 can perform the at least one function in a second mode.

According to various embodiments, in the case where the medical policy satisfies the first condition, the processor 120 can perform a first set of functions among functions of the application as the at least one function. In the case where the medical policy satisfies the second condition, the processor 120 can perform a second set of functions among the functions as the at least one function.

According to various embodiments, the medical service app 210 can include a first application and a second application. In the case where the medical policy satisfies the first condition, the processor 120 can perform a function of the first application as the at least one function. In the case where the medical policy satisfies the second condition, the processor 120 can perform a function of the second application as the at least one function. According to various embodiments, the second condition can include the case where the first condition is not satisfied.

Figure 3B:
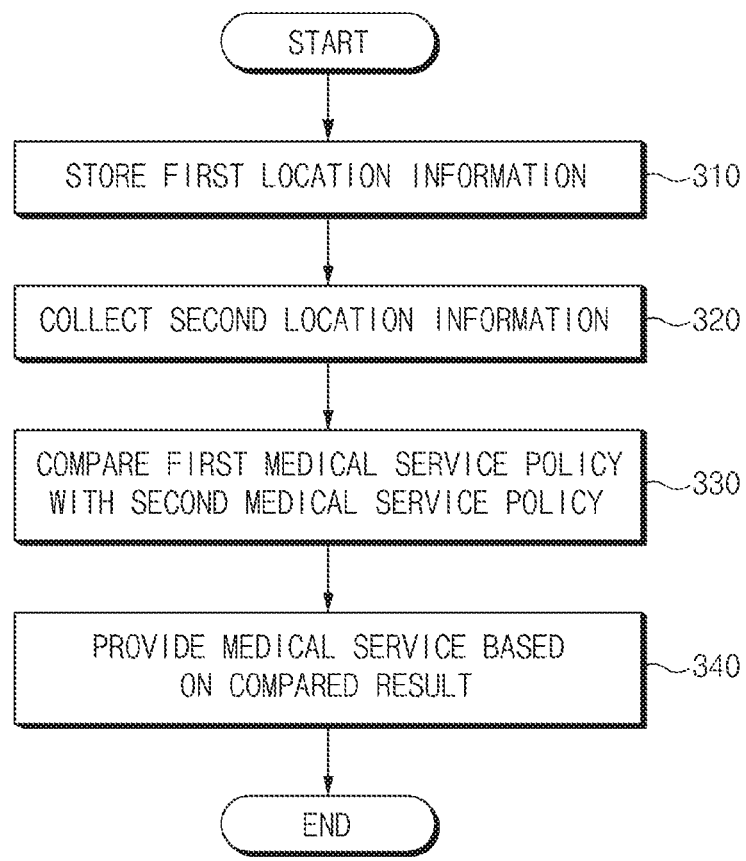

FIG. 3B is a flowchart for describing a method for providing a medical service, according to various embodiments.

Referring to FIG. 3B, in operation 310, the processor 120 (e.g., the medical service module 180) can store information about a first location (hereinafter called "first location information") at which a user has performed a medical service before. The first location information can include one or more of local information such as a nation, an administrative district, and a road name, in which the user has received the medical service before, or absolute location information such as latitude/longitude.

According to various embodiments, the processor 120 can store information about a medical service policy at a time when the user receives the medical service in the first location, and user medical information (e.g., biometric recognition information, a physical exam, prescription, or the like) together with the first location information.

In operation 320, the processor 120 can collect information about a second location (hereinafter called "second location information") at which the user performs the medical service. According to various embodiments, the second location can be a place that is away from the first location by a specified distance or more. The first location and the second location can be locations to which different medical service policies are applied, respectively. Like the first location information, the second location information can include one or more of local information or absolute location information.

In various embodiments, the processor 120 can collect location information (current location information of the user or information about a location to which the user is scheduled to move) of the electronic device 101 by using the communication module 170, the sensor module 190, or content (e.g., content extracted from an airline ticket, a theater ticket, a hotel reservation confirmation letter, or the like or information extracted from a schedule app).

The user can move to a location due to a travel, a business trip, or the like and can receive a medical service, which is the same or similar to a medical service provided in a previous place (a first location), in a place (a second location) to which the user moves. However, in this case, a medical service policy for performing the medical service can be changed according to a location of the user. The user can perform a telemedicine service within a range of a medical service policy changed according to a guide that the electronic device 101 provides, thereby reducing the inconvenience of deciding each medical service policy.

In operation 330, the processor 120 can compare a first medical service policy, which is based on first location information, with a second medical service policy that is based on the second location information.

In operation 340, the processor 120 can provide the user with the medical service based on a compared result.

FIG. 4 is a drawing illustrating a change in a medical service policy based on movement of a user, according to various embodiments.

Referring to FIG. 4, a user 401 can move from a first area 410 to a second area 420. Before the user 401 moves to the second area 420, the user 401 can have a medical record of performing a medical service in the first area 410. In the first area 410, a first medical service policy 411 for performing the medical service can be applied thereto.

For example, in the first area 410, a medical service policy can require the followings: 1) there should be a medical record of directly visiting a doctor and receiving the medical service, 2) performing the medical service through a voice call or a video call, 3) receiving a signature of agreement for performing the medical service, and the like.

The processor 120 (e.g., the medical service module 180) can store first location information and, in some cases, can store the first medical service policy and user medical information (e.g., biometric information, a physical exam, a prescription, or the like) at a time when the user receives the medical service.

In the case where the user 401 moves to the second area 420, the medical service policy to be applied can vary in the second area 420. The electronic device 101 can collect second location information by using a sensor module, a communication module, or content (e.g., content extracted from an airline ticket, a theater ticket, a hotel reservation confirmation letter, or the like or information extracted from a schedule app). The electronic device 101 can search for a second medical service policy 421, which is applied in the second area 420, based on the second location information. For example, in the case where a medical service policy in the second area 420 is stored in an embedded memory of the electronic device 101, the electronic device 101 can refer to the stored medical service policy. As another example, in the case where the second medical service policy 421 in a second location is not stored therein or where the second medical service policy 421 in the second location needs to be updated even though the second medical service policy 421 in the second location is stored, the electronic device 101 can search for the second medical service policy 421 by using an external device (e.g., the medical service policy server 106). The electronic device 101 can send the second location information to the external device (e.g., the medical service policy server 106) and can request the external device to send a medical service policy, which will be applied in the second location, to the electronic device 101.

For example, in the second area 420, a medical service policy can require the followings: 1) the user should be within a specified distance from a doctor who will perform the medical service, 2) performing the medical service through a video call, 3) receiving an offline signature for performing the medical service of the user, and the like.

The processor 120 (e.g., the medical service module 180) can compare the first medical service policy 411 with the second medical service policy 421 and can decide a condition for performing the medical service in the second area 420 based on the compared result. The electronic device 101 can provide a guide on operations, which are necessary for the user 401 to perform the medical service in the second area 420, based on the compared result.

According to various embodiments, in the case where the first medical service policy 411 in the first area 410 is the same as the second medical service policy 421 in the second area 420, the processor 120 (e.g., the medical service module 180) can perform the medical service without notifying the user 401, or can notify the user 401 that the electronic device 101 is capable of performing the medical service and can perform the medical service.

FIG. 5 illustrates a table for a medical policy changed according to an area, according to various embodiments. FIG. 5 can be an example, and embodiments are not limited thereto.

Referring to FIG. 5, the electronic device 101 can store a medical service policy table 501. The electronic device 101 can search for the stored medical service policy table 501 by using location information of a user or the electronic device 101. The electronic device 101 can decide a condition for performing a medical service based on the found medical service policy and can notify the user of the condition.

In an embodiment, the electronic device 101 can store a table including all medical service policies for administrative districts of a specific nation. In the case where the electronic device 101 performs the medical service, the electronic device 101 can refer to the stored table. The electronic device 101 can periodically update the medical service policy table 501. In another embodiment, the electronic device 101 can store a table including medical service policies of places at which the user has performed the medical service before. As the number of times that the medical service is performed increases, the electronic device 101 can database and store a medical service policy, which has been applied before, together with location information.

The medical service policy table 501 can include first to fifth conditions 510 to 550 for performing the medical service in each area. The first to fifth conditions are illustrated in FIG. 5. However, embodiments are not limited thereto.

For example, in Alabama state, conditions can requires the followings: 1) there should be a previous physical exam (510), 2) there should be a medical record of directly visiting a doctor before (520), 3) there should be informed consent (530), 4) there should be participation of a telepresenter (540), and 5) a medical service is provided with an out-of-state doctor license (550).

In Alaska state, conditions can require the followings: 1) there should be a previous physical exam (510), 2) there should be a medical record of directly visiting a doctor before (520), 3) there should be participation of a telepresenter (540), and 4) a medical service is provided with an out-of-state doctor license (550).

In the case where the user moves from Alabama state to Alaska state and performs the medical service, the electronic device 101 can compare the medical service policy in Alabama state with the medical service policy in Alaska state and can decide the difference in "there should be informed consent" (530), based on the compared result.

In the case where the electronic device 101 performs the medical service in Alabama state, the electronic device 101 can allow the user not to care about the changed medical service policy by omitting a process of receiving informed consent such as an electronic signature, or the like.

Figure 6:
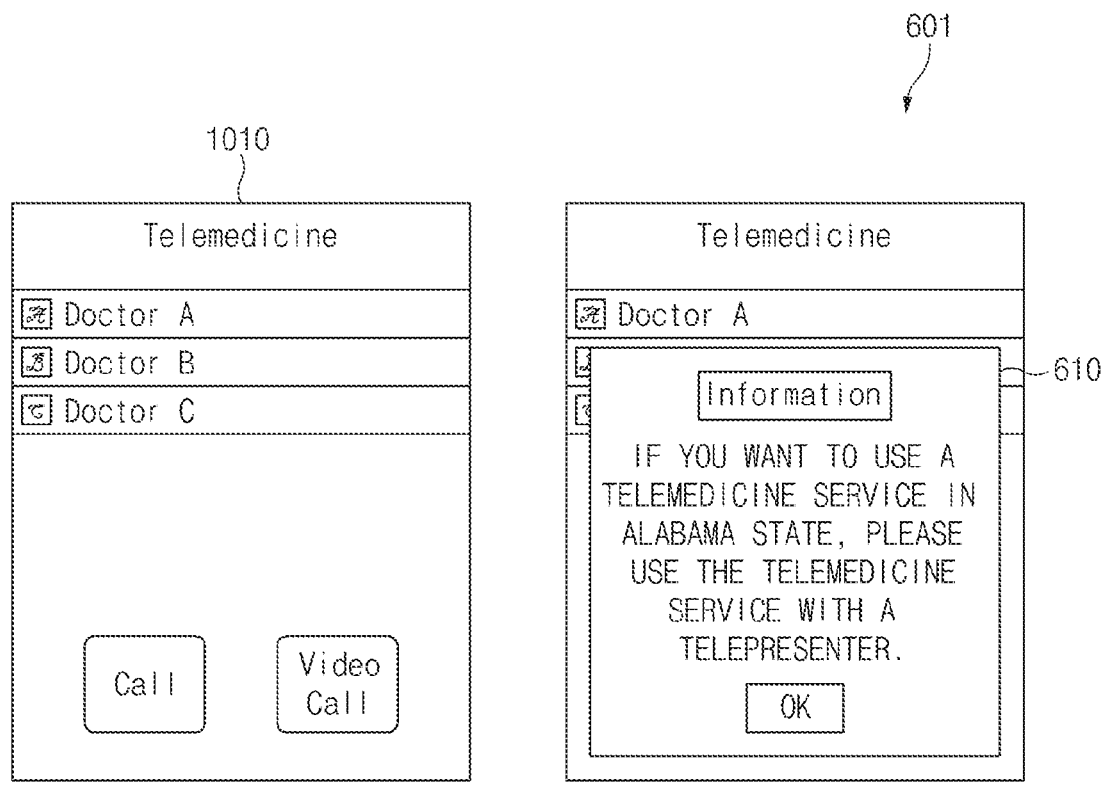
FIG. 6 is a drawing of a medical service app that performs a medical service, according to various embodiments.

FIG. 6 is a drawing of a medical service app that performs a medical service, according to various embodiments. FIG. 6 can be an example, and embodiments are not limited thereto.

Referring to FIG. 6, the electronic device 101 can output an execution screen 601 by driving the medical service app 210 in FIG. 2. For example, in the execution screen 601, a user can decide a list of doctors that are capable of providing the medical service and can select a doctor that performs the medical service.

According to various embodiments, in the case where the medical service app 210 is driven, the electronic device 101 can automatically collect current location information of the electronic device 101 by using a sensor module or a communication module of the electronic device 101. The electronic device 101 can decide a medical service policy at a corresponding location based on the collected location information.

In the process of performing a medical service based on a medical service policy applied in the corresponding area, the electronic device 101 can provide notification of a policy that the user should know, a policy that should be performed differently from a previous medical service, or the like through a pop-up box 610. The user can decide content in the pop-up box 610 and can take an action based on the decided content. In FIG. 5, it is exemplarily illustrated that a message for requesting a telepresenter to participate in the medical service is output to the user. However, embodiments are not limited thereto. For example, in the case where an electronic signature is needed, the medical service app 210 can output an input screen for entering an electronic signature, a screen for authorized certification, or the like.

Figure 7:
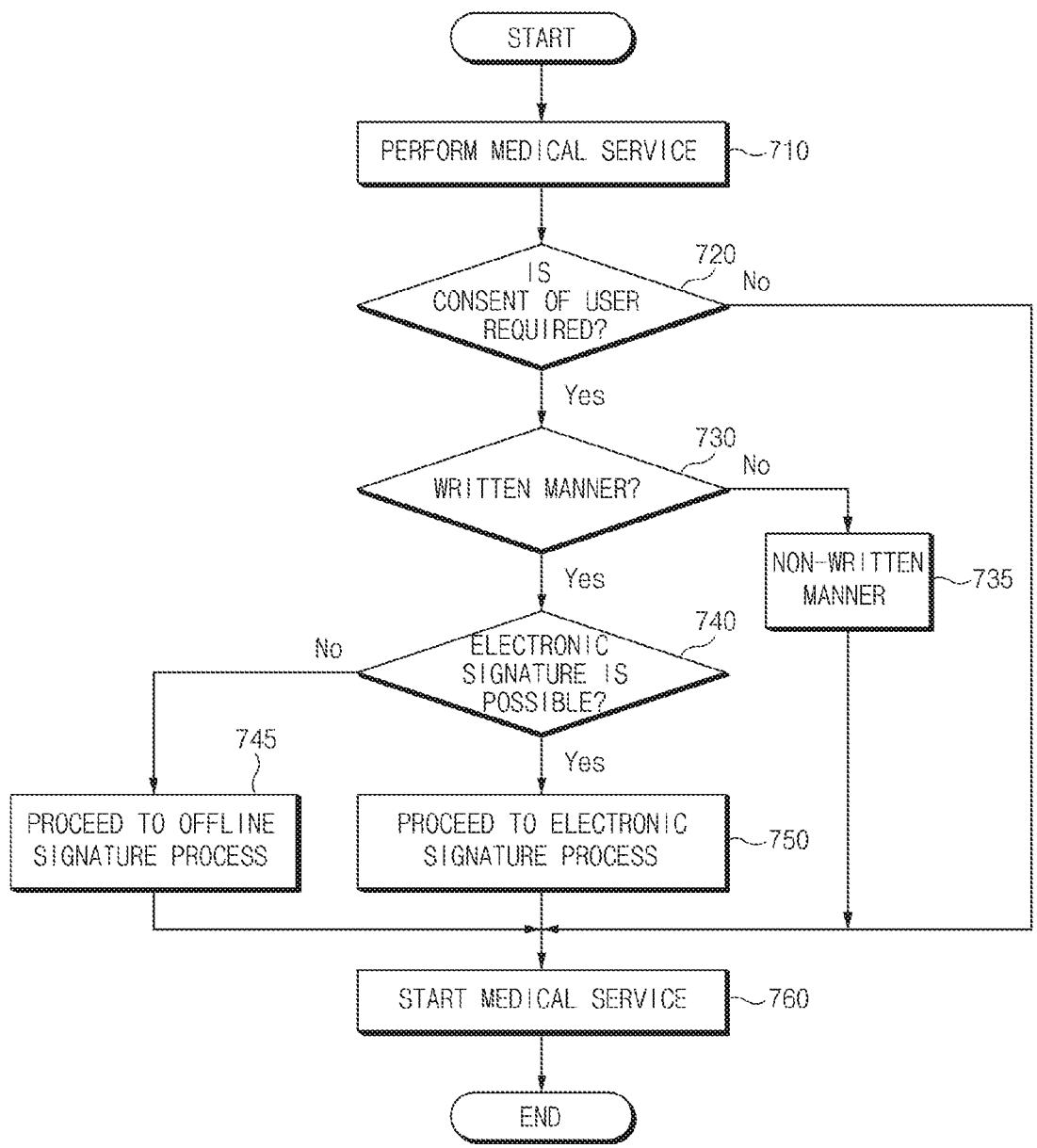
FIG. 7 is a flowchart for describing a process in which a user agrees to a medical service, according to various embodiments.

FIG. 7 is a flowchart for describing a process in which a user agrees to a medical service, according to various embodiments.

Referring to FIG. 7, in operation 710, the electronic device 101 can perform a medical service in response to a request of the user. The electronic device 101 can perform the medical service app 210 and can collect current location information of the user or information about a location to which the user moves. The electronic device 101 can decide a medical service policy applied to a current location or a location, to which the user will move in the future, based on the collected location information.

In operation 720, the electronic device 101 can determine whether a policy for performing a medical service requires consent of the user at a corresponding location. The consent of the user can be performed in various manners. Hereinafter, an embodiment is exemplified as an offline signature, an electronic signature, or a non-written signature. However, embodiments are not limited thereto.

In operation 730, the electronic device 101 can determine whether the consent of the user that a medical service policy requires is in a written manner. The written manner can include a direct signature of the user offline or an electronic signature on a touch screen.

In operation 735, in the case where the consent of the user is in a non-written manner such as voice consent, or the like, the electronic device 101 can be ready to receive a signature corresponding to a corresponding manner. For example, the electronic device 101 can turn on a microphone and can stand by to receive the voice consent of the user.

In operation 740, the electronic device 101 can determine whether the consent of the user is possible by using an electronic signature.

In operation 745, the electronic device 101 can proceed to an offline signature process. For example, the electronic device 101 can explain a method (e.g., downloading a form for a signature and sending the form, which is signed, to a hospital by fax or email) for an offline signature to the user. The electronic device 101 can display a uniform resource locater (URL) for downloading the form.

In operation 750, the electronic device 101 can proceed to an electronic signature process. For example, the electronic device 101 can output a screen including an input field for an electronic signature, and the user can agree to the medical service by signing by using a touch input in the input field.

In operation 760, in the case where a signature of the user is completed, the electronic device 101 can start a medical service. According to various embodiments, in the case where an operation is needed according to a medical service policy even though a medical service is being performed, the electronic device 101 can perform the operation.

Figure 8:
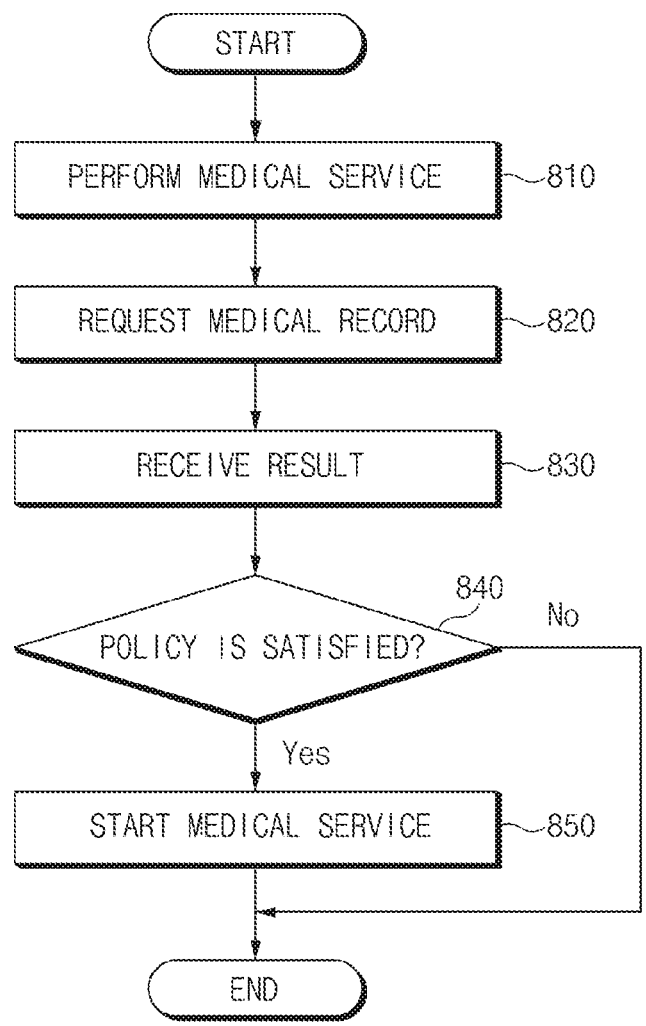
FIG. 8 is a flowchart illustrating processing a policy that requires a medical record of a user, according to various embodiments.

FIG. 8 is a flowchart illustrating processing a policy that requires a medical record of a user, according to various embodiments.

Referring to FIG. 8, in operation 810, the electronic device 101 can perform a medical service in response to a request of the user. The electronic device 101 can perform the medical service app 210 and can collect information about current location information of the user or a location to which the user will move. The electronic device 101 can decide a medical service policy applied at a current location or a location, to which the user will move in the future, based on the collected location information. The electronic device 101 can determine whether a policy for performing the medical service at a corresponding location requires the medical record by visiting a doctor or a hospital.

In operation 820, in the case where the corresponding policy requires a previous medical record, the electronic device 101 can request a medical record of the user from an external device (e.g., the medical service providing device 104 in FIG. 1). The electronic device 101 can send identification information (e.g., an electronic signature or a certificate digital signature) of the user to the external device, can perform authentication by using the identification information of the user, and can request the external device to search for the medical record.

In operation 830, the electronic device 101 can receive the result obtained by searching for the medical record of the user from the external device.

In operation 840, the electronic device 101 can determine whether the medical service is possible, based on the found medical record of the user. In the case where the medical record of the user is not found, the electronic device 101 can notify the user of the result and can end the medical service.

In operation 850, in the case where the found medical record of the user satisfies the policy, the electronic device 101 can start the medical service.

Figure 9:
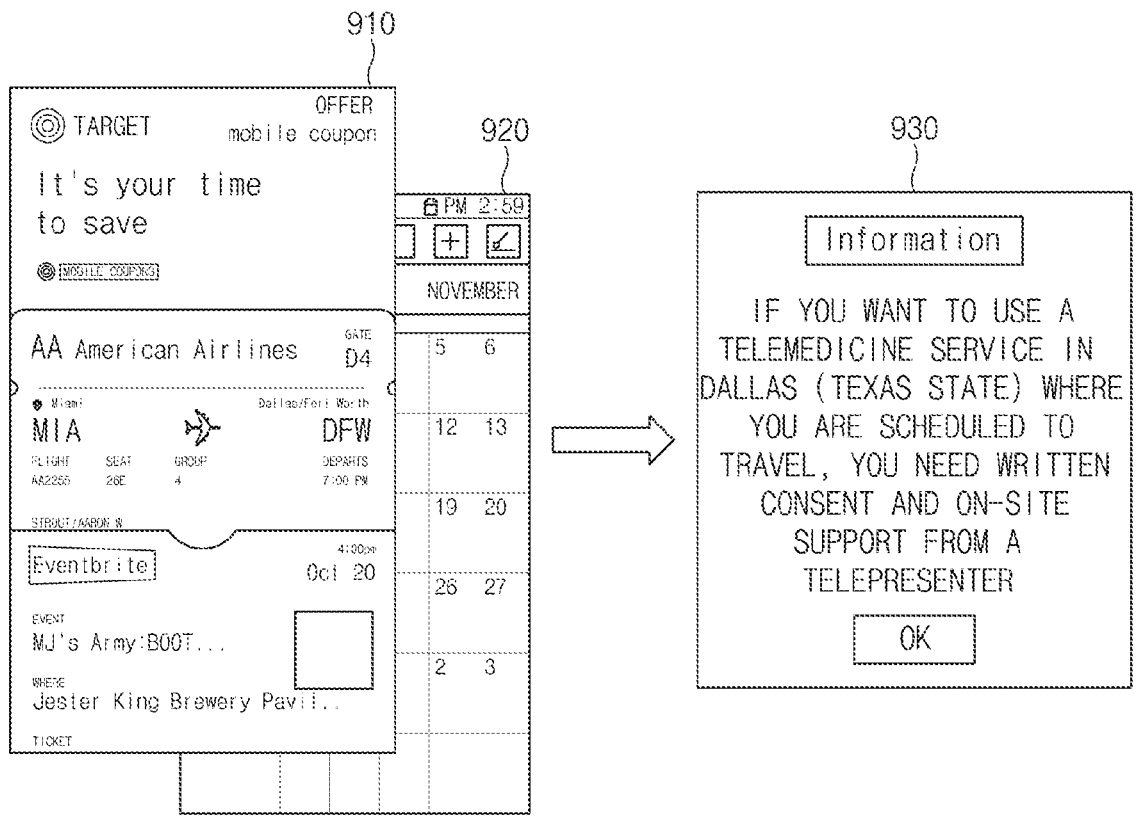
FIG. 9 is a drawing for describing extraction of location information based on a schedule of a user, according to various embodiments.

FIG. 9 is a drawing for describing extraction of location information based on a schedule of a user, according to various embodiments.

Referring to FIG. 9, the electronic device 101 can collect information about a location, to which the user will move in the future, through various applications. For example, the electronic device 101 can collect information about the time and place, when and where the user will move, from a mobile ticket 910 such as an airline ticket or a movie ticket. As another example, the electronic device 101 can collect information about the time and place, when and where the user will move, by using schedule information of the user stored in a schedule application 920.

If the collected schedule of the user approaches, the electronic device 101 can notify the user of a condition, which is necessary to perform the medical service at a corresponding place, through a pop-up 930. The user can decide the necessary condition in advance at a place, to which the user will move in the future, and can be ready to perform the medical service in advance at a corresponding place. In FIG. 9, it is exemplarily illustrated that the electronic device 101 notifies the user of the necessary condition in the form of the pop-up box 930. However, embodiments are not limited thereto. For example, the electronic device 101 can allow the user to complete agreement to the medical service in advance, by outputting a screen for receiving informed consent from the user in advance.

Figure 10:
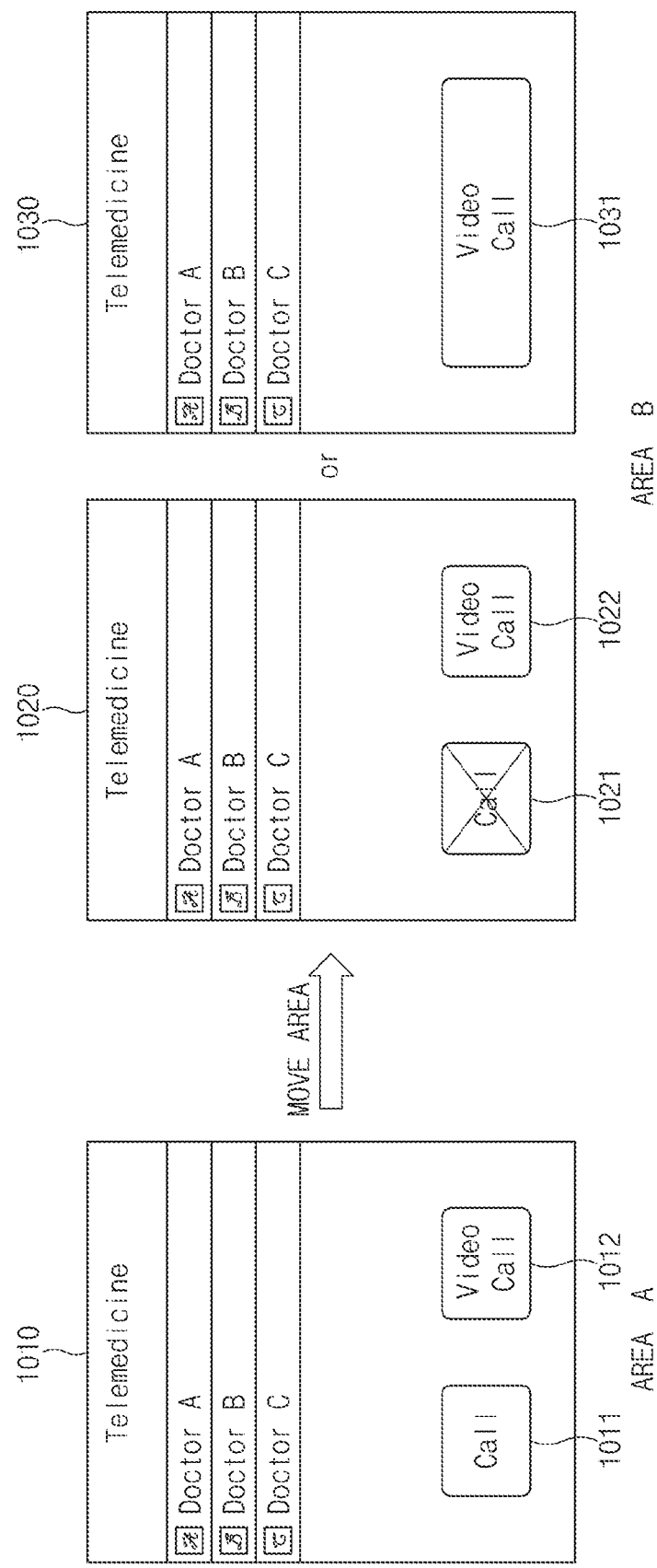
FIG. 10 is a drawing for describing activating or deactivating a function of an electronic device based on a medical service policy, according to various embodiments.

FIG. 10 is a drawing for describing activating or deactivating a function of an electronic device based on a medical service policy, according to various embodiments.

Referring to FIG. 10, the electronic device 101 can perform a medical service in response to a request of a user. The electronic device 101 can perform the medical service app 210 and can collect current location information of the user or information about a location to which the user will move. The electronic device 101 can decide a medical service policy applied at a current location or a location, to which the user will move in the future, based on the collected location information.

The electronic device 101 can output an execution screen 1010 by driving the medical service app 210. The electronic device 101 can activate or deactivate a part of function based on the applied policy.

For example, in area A, in the case where the electronic device 101 performs the medical service, the electronic device 101 can be configured such that both a voice call button 1011 and a video call button 1012 are activated according to a policy in area A. In this case, the user can select one of a voice call or a video call and can perform the medical service based on the selected result.

In the case where the user moves to area B and performs the medical service, the medical service through the voice call can be restricted according to a policy in area B. In this case, the electronic device 101 can allow the user to fail to perform a voice call function by outputting an execution screen 1020 or 1030 in which the voice call function is restricted. In the execution screen 1020, the electronic device 101 can allow a voice call button 1021 to be deactivated and can allow a video call button 1022 to be activated. In the execution screen 1030, the electronic device 101 can allow a voice call button to disappear on a screen and can allow only a video call button 1031 to be output. The user can easily perform the medical service through a screen automatically changed according to a medical service policy in an area to which the user will move.

According to various embodiments, the processor 120 can determine whether a premise based on the medical service policy is satisfied.

For example, in the case where the determined medical service policy requires that a distance between a medical service provider (e.g., a hospital or a doctor) and a patient is within a specified distance (e.g., within 100 m, in the same building, or the like), the processor 120 can determine whether the distance between the medical service provider and the patient is within the specified distance, by comparing a location (e.g., a location of a hospital, a location of a hospital server, a location of a personal terminal of a doctor, or the like) of the medical service provider with a location of the electronic device 101 (or the user using the electronic device 101) in real time.

In the case where the distance between the medical service provider and the patient is within the specified distance, the processor 120 can provide the medical service to the user. On the other hand, in the case where the distance between the medical service provider and the patient is beyond the specified distance, the processor 120 can notify the user that the premise for the medical service is not satisfied and can guide the user to move to a location for performing the medical service.

In an embodiment, the processor 120 can request location information from an external device (e.g., a hospital server or a doctor personal terminal). The processor 120 can determine whether a premise is satisfied, by comparing location information received from the external device with the location information recognized through the sensor module 190 of the electronic device 101.

In another embodiment, the processor 120 can send location information recognized through the sensor module 190 of the electronic device 101 to an external device (e.g., a hospital server) and can determine whether a premise is satisfied. The processor 120 can receive the result from an external device and can provide the medical service based on the received result.

According to various embodiments, in the process of providing the medical service, the processor 120 can perform a separate authentication process. For example, the processor 120 can perform the separate authentication process to send or verify information, which is necessary to provide the medical service, such as a medical record of the user, the measured heart rate information, location information, or the like. As another example, in the case where the medical service app is executed, the processor 120 can allow only the user specified through an authentication process (e.g., fingerprint recognition, iris recognition, entering a password, or the like) to perform the corresponding medical service app.

According to various embodiments, the processor 120 can change or generalize (abstract) health information of the user and can send the changed or generalized health information of the user to the external device. For example, in the case where the user performs the medical service app, the processor 120 can send only a portion (e.g., a man in his twenties, resident in Seoul, having a heart disease, data of heart rate information in some of intervals, or the like) of personal information of the user (e.g., gender, age, a residential district, a body characteristic) to the external device. Accordingly, possibility that personal information of the user is leaked to the outside can be reduced.

According to various embodiments, the processor 120 can provide the user with a UI screen for determining the degree of change or generalization of information that is necessary to perform the medical service. The processor 120 can determine the degree of change or generalization of the information based on a user input and can perform the medical service based on the determined result. For example, the processor 120 can maintain data change at a level, which satisfies the determined medical service policy, at default settings. In the case where the user requests the data change beyond the medical service policy, the processor 120 can notify the user that the medical service is restricted.

According to various embodiments, the processor 120 can determine necessary information to be sent to the external device based on the determined medical service policy. For example, the processor 120 can send only the necessary information (e.g., data of heart rate information in some of intervals, hospital medical information within a specified interval, or the like), which is needed to perform the medical service, from among health information (e.g., physical information, heart rate information, or the like) of the user to the external device (e.g., a hospital server or a doctor personal terminal). The necessary information can be distinguished based on a collection time period, an amount of data, or the like within a corresponding time period or within a corresponding data range, and can be sent to the external device (e.g., a hospital server or a doctor personal terminal).

According to various embodiments, in the case where additional information beyond a range of the necessary information is requested from the external device, the processor 120 can automatically restrict the transmission of the additional information or can provide the user with a UI screen (e.g., a pop-up box) for determining whether the additional information is sent.

According to various embodiments, a medical service providing method performed by an electronic device, the method can include obtaining a request for execution of an application that provides a medical service, deciding a medical policy, which corresponds to a location of the electronic device, from among one or more medical policies and selectively providing at least one function of the application based on a medical service performing method, which is determined based at least on the medical policy, from among one or more medical service performing methods.

According to various embodiments, the deciding of the medical policy can include obtaining information about the location by using a communication module or a sensor module included in the electronic device.

According to various embodiments, the deciding of the medical policy can include extracting a location, to which a user is scheduled to move, based at least on schedule information stored in a memory of the electronic device and determining a location of the electronic device.

According to various embodiments, the deciding of the medical policy can include selecting a telemedicine policy of the one or more medical policies as at least a part of the medical policy.

According to various embodiments, the deciding of the medical policy can include receiving at least some of the one or more medical policies from an external electronic device by using a communication module included in the electronic device.

According to various embodiments, the selectively providing of the at least one function of the application can include performing the at least one function if the medical policy satisfies a first condition and refraining from performing the at least one function if the medical policy satisfies a second condition.

According to various embodiments, the selectively providing of the at least one function of the application can include performing the at least one function in a first mode if the medical policy satisfies a first condition and performing the at least one function in a second mode if the medical policy satisfies a second condition.

According to various embodiments, the selectively providing of the at least one function of the application can include performing a first set of functions among functions of the application as the at least one function if the medical policy satisfies a first condition and performing a second set of functions among the functions as the at least one function if the medical policy satisfies a second condition.

Figure 11:
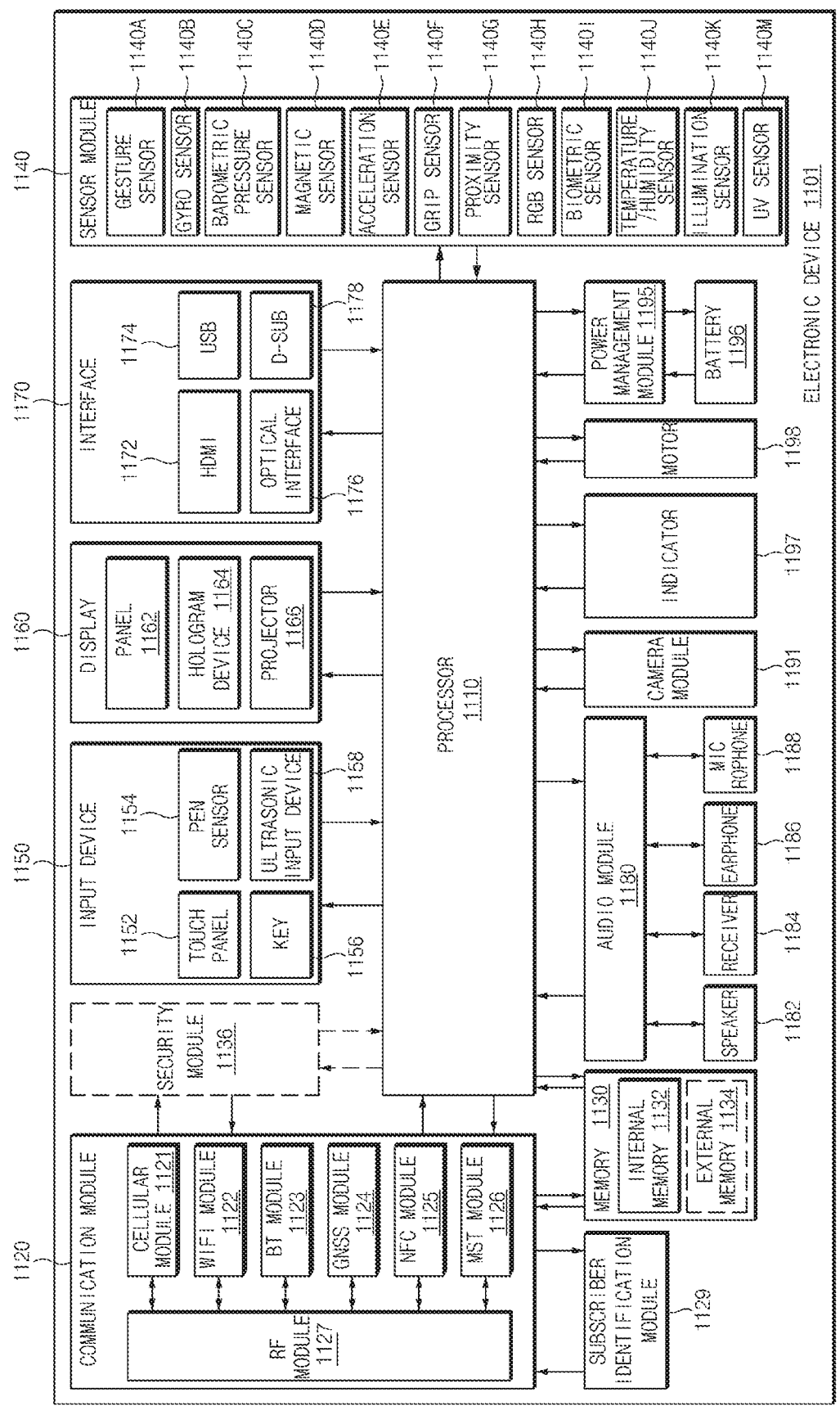
FIG. 11 illustrates a block diagram of an electronic device according to various embodiments.

FIG. 11 is a block diagram of an electronic device according to various embodiments. An electronic device 1101 cancan include, for example, all or a part of the electronic device 111 illustrated in FIG. 1. The electronic device 1101 cancan include one or more processors (e.g., an application processor (AP)) 1110, a communication module 1120, a subscriber identification module 1124, a memory 1130, a sensor module 1140, an input device 1150, a display 1160, an interface 1170, an audio module 1180, a camera module 1191, a power management module 1195, a battery 1196, an indicator 1197, and a motor 1198.

The processor 1110 cancan drive an operating system (OS) or an application to control a plurality of hardware or software elements connected to the processor 1110 and can process and compute a variety of data. The processor 1110 can be implemented with a System on Chip (SoC), for example. According to an embodiment, the processor 1110 can further include a graphic processing unit (GPU) and/or an image signal processor. The processor 1110 can include at least a part (e.g., a cellular module 1121) of elements illustrated in FIG. 11. The processor 1110 can load and process an instruction or data, which is received from at least one of other elements (e.g., a nonvolatile memory) and can store a variety of data in a nonvolatile memory.

The communication module 1120 can be configured the same as or similar to the communication interface 170 of FIG. 1. The communication module 1120 can include a cellular module 1121, a Wi-Fi module 1123, a Bluetooth (BT) module 1125, a GNSS module 1127 (e.g., a GPS module, a Glonass module, a Beidou module, or a Galileo module), a near field communication (NFC) module 1128, and a radio frequency (RF) module 1129.

The cellular module 1121 can provide voice communication, video communication, a message service, an Internet service or the like through a communication network. According to an embodiment, the cellular module 1121 can perform discrimination and authentication of the electronic device 1101 within a communication network using the subscriber identification module 1124 (e.g., a SIM card), for example. According to an embodiment, the cellular module 1121 can perform at least a portion of functions that the processor 1110 provides. According to an embodiment, the cellular module 1121 can include a communication processor (CP).

Each of the Wi-Fi module 1123, the BT module 1125, the GNSS module 1127, and the NFC module 1128 can include a processor for processing data exchanged through a corresponding module, for example. According to an embodiment, at least a part (e.g., two or more elements) of the cellular module 1121, the Wi-Fi module 1123, the BT module 1125, the GNSS module 1127, or the NFC module 1128 can be included within one Integrated Circuit (IC) or an IC package.

The RF module 1129 can transmit and receive, for example, a communication signal (e.g., an RF signal). The RF module 1129 can include, for example, a transceiver, a power amplifier module (PAM), a frequency filter, a low noise amplifier (LNA), an antenna, or the like. According to another embodiment, at least one of the cellular module 1121, the Wi-Fi module 1123, the BT module 1125, the GNSS module 1127, or the NFC module 1128 can transmit and receive an RF signal through a separate RF module.

The subscriber identification module 1124 can include, for example, a card and/or embedded SIM that includes a subscriber identification module and can include unique identify information (e.g., integrated circuit card identifier (ICCID)) or subscriber information (e.g., international mobile subscriber identity (IMSI)).

The memory 1130 (e.g., the memory 130) can include an internal memory 1132 or an external memory 1134. For example, the internal memory 1132 can include at least one of a volatile memory (e.g., a dynamic random access memory (DRAM), a static RAM (SRAM), or a synchronous DRAM (SDRAM)), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, or a NOR flash memory), a hard drive, or a solid state drive (SSD).

The external memory 1134 can include a flash drive, for example, compact flash (CF), secure digital (SD), micro secure digital (Micro-SD), mini secure digital (Mini-SD), extreme digital (xD), multimedia card (MMC), a memory stick, or the like. The external memory 1134 can be functionally and/or physically connected with the electronic device 1101 through various interfaces.

The sensor module 1140 can measure, for example, a physical quantity or can detect an operation state of the electronic device 1101. The sensor module 1140 can convert the measured or detected information to an electric signal. The sensor module 1140 can include at least one of a gesture sensor 1140A, a gyro sensor 1140B, a barometric pressure sensor 1140C, a magnetic sensor 1140D, an acceleration sensor 1140E, a grip sensor 1140F, a proximity sensor 1140G, a color sensor 1140H (e.g., red, green, blue (RGB) sensor), a biometric sensor 1140I, a temperature/humidity sensor 1140J, an illuminance sensor 1140K, or an UV sensor 1140M. Even though not illustrated, additionally or alternatively, the sensor module 1140 can include, for example, an E-nose sensor, an electromyography sensor (EMG) sensor, an electroencephalogram (EEG) sensor, an electrocardiogram (ECG) sensor, an infrared (IR) sensor, an iris sensor, and/or a fingerprint sensor. The sensor module 1140 can further include a control circuit for controlling at least one or more sensors included therein. According to an embodiment, the electronic device 1101 can further include a processor which is a part of the processor 1110 or independent of the processor 1110 and is configured to control the sensor module 1140. The processor can control the sensor module 1140 while the processor 1110 remains at a sleep state.

The input device 1150 can include, for example, a touch panel 1152, a (digital) pen sensor 1154, a key 1156, or an ultrasonic input unit 1158. The touch panel 1152 can use at least one of capacitive, resistive, infrared and ultrasonic detecting methods. Also, the touch panel 1152 can further include a control circuit. The touch panel 1152 can further include a tactile layer to provide a tactile reaction to a user.

The (digital) pen sensor 1154 can be, for example, a portion of a touch panel or can include an additional sheet for recognition. The key 1156 can include, for example, a physical button, an optical key, a keypad, or the like. The ultrasonic input device 1158 can detect (or sense) an ultrasonic signal, which is generated from an input device, through a microphone (e.g., a microphone 1188) and can check data corresponding to the detected ultrasonic signal.

The display 1160 (e.g., the display 160) can include a panel 1162, a hologram device 1164, or a projector 1166. The panel 1162 can be configured the same as or similar to the display 160 of FIG. 1. The panel 1162 can be implemented to be flexible, transparent or wearable, for example.

The panel 1162 and the touch panel 1152 can be integrated into a single module. The hologram device 1164 can display a stereoscopic image in a space using a light interference phenomenon. The projector 1166 can project light onto a screen so as to display an image. The screen can be arranged inside or outside the electronic device 1101. According to an embodiment, the display 1160 can further include a control circuit for controlling the panel 1162, the hologram device 1164, or the projector 1166.

The interface 1170 can include, for example, a high-definition multimedia interface (HDMI) 1172, a universal serial bus (USB) 1174, an optical interface 1176, or a D-subminiature (D-sub) 1178. The interface 1170 can be included, for example, in the communication interface 170 illustrated in FIG. 1. Additionally or alternatively, the interface 1170 can include, for example, a mobile high definition link (MHL) interface, a SD card/multi-media card (MMC) interface, or an infrared data association (IrDA) standard interface.

The audio module 1180 can convert a sound and an electrical signal in dual directions. At least a part of the audio module 1180 can be included, for example, in the input/output interface 150 illustrated in FIG. 1. The audio module 1180 can process, for example, sound information that is input or output through a speaker 1182, a receiver 1184, an earphone 1186, or a microphone 1188.

The camera module 1191 for shooting a still image or a video can include, for example, at least one image sensor (e.g., a front sensor or a rear sensor), a lens, an image signal processor (ISP), or a flash (e.g., an LED or a xenon lamp).

The power management module 1195 can manage, for example, power of the electronic device 1101. According to an embodiment, a power management integrated circuit (PMIC) a charger IC, or a battery or fuel gauge can be included in the power management module 1195. The PMIC can have a wired charging method and/or a wireless charging method. The wireless charging method can include, for example, a magnetic resonance method, a magnetic induction method or an electromagnetic method and can further include an additional circuit, for example, a coil loop, a resonant circuit, a rectifier, or the like. The battery gauge can measure, for example, a remaining capacity of the battery 1196 and a voltage, current or temperature thereof while the battery is charged. The battery 1196 can include, for example, a rechargeable battery or a solar battery.

The indicator 1197 can display a specific state of the electronic device 1101 or a part thereof (e.g., the processor 1110), such as a booting state, a message state, a charging state, and the like. The motor 1198 can convert an electrical signal into a mechanical vibration and can generate a vibration effect, a haptic effect, or the like. Even though not illustrated, a processing device (e.g., a GPU) for supporting a mobile TV can be included in the electronic device 1101. The processing device for supporting a mobile TV can process media data according to the standards of digital multimedia broadcasting (DMB), digital video broadcasting (DVB), MediaFlo®, or the like.

Each of the above-mentioned elements can be configured with one or more components, and the names of the elements can be changed according to the type of the electronic device. The electronic device according to various embodiments can include at least one of the above-mentioned elements, and some elements can be omitted or other additional elements can be added. Furthermore, some of the elements of the electronic device according to various embodiments can be combined with each other so as to form one entity, so that the functions of the elements can be performed in the same manner as before the combination.

Figure 12:
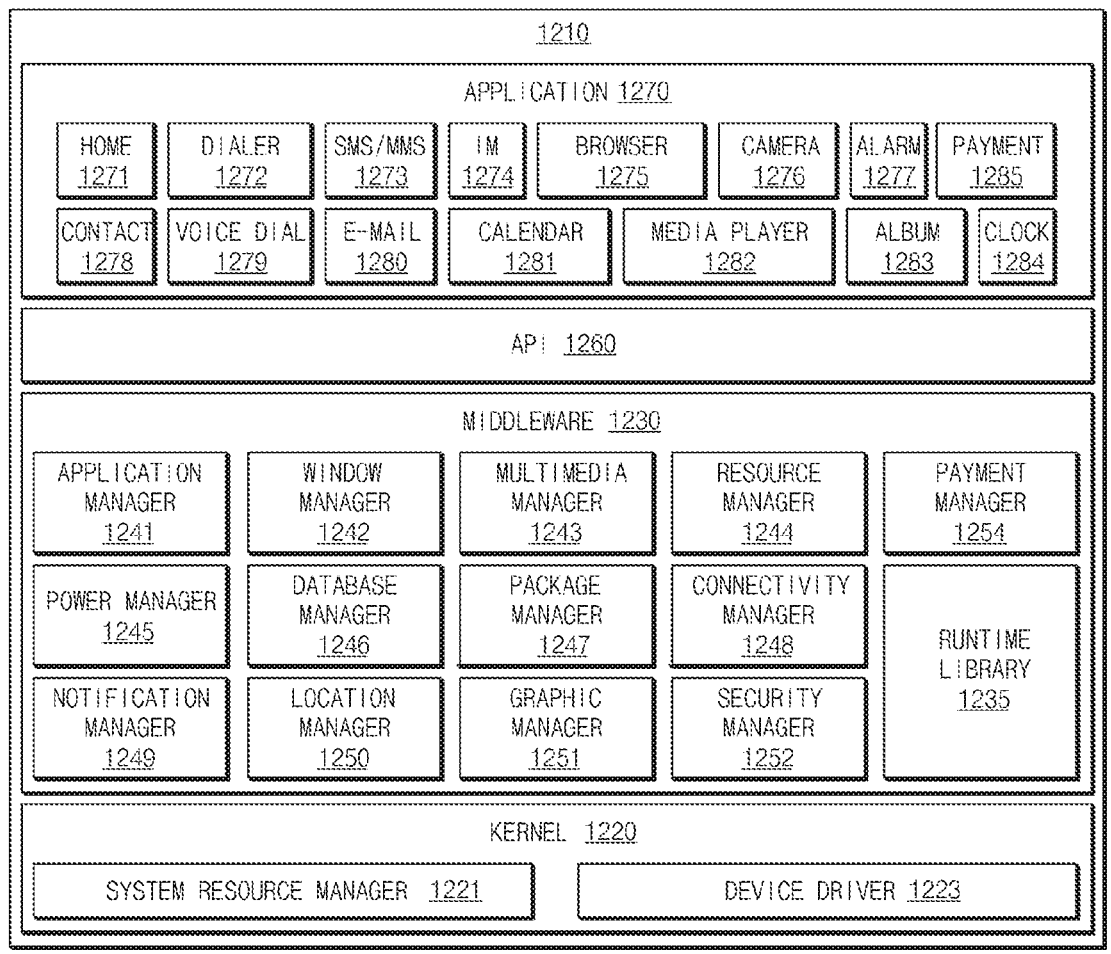
FIG. 12 illustrates a block diagram of a program module, according to various embodiments.

FIG. 12 is a block diagram of a program module according to various embodiments. According to an embodiment, a program module 1210 (e.g., the program 140) can include an operating system (OS) to control resources associated with an electronic device (e.g., the electronic device 101) and/or diverse applications (e.g., the application program 147) driven on the OS. The OS can be, for example, android®, iOS®, windows®, symbian®, tizen®, or bada®.

The program module 1210 can include a kernel 1220, a middleware 1230, an application programming interface (API) 1260, and/or an application 1270. At least a part of the program module 1210 can be preloaded on an electronic device or can be downloadable from an external electronic device (e.g., the external device 102, and the like).

The kernel 1220 (e.g., the kernel 141) can include, for example, a system resource manager 1221 and/or a device driver 1223. The system resource manager 1221 can perform control, allocation, or retrieval of system resources. According to an embodiment, the system resource manager 1221 can include a process managing part, a memory managing part, or a file system managing part. The device driver 1223 can include, for example, a display driver, a camera driver, a Bluetooth driver, a shared memory driver, an USB driver, a keypad driver, a Wi-Fi driver, an audio driver, or an inter-process communication (IPC) driver.

The middleware 1230 can provide, for example, a function which the application 1270 needs in common, or can provide diverse functions to the application 1270 through the API 1260 to allow the application 1270 to efficiently use limited system resources of the electronic device. According to an embodiment, the middleware 1230 (e.g., the middleware 143) can include at least one of a runtime library 1235, an application manager 1241, a window manager 1242, a multimedia manager 1243, a resource manager 1244, a power manager 1245, a database manager 1246, a package manager 1247, a connectivity manager 1248, a notification manager 1249, a location manager 1250, a graphic manager 1251, or a security manager 1252.

The runtime library 1235 can include, for example, a library module which is used by a compiler to add a new function through a programming language while the application 1270 is being executed. The runtime library 1235 can perform input/output management, memory management, or capacities about arithmetic functions.

The application manager 1241 can manage, for example, a life cycle of at least one application of the application 1270. The window manager 1242 can manage a GUI resource which is used in a screen. The multimedia manager 1243 can identify a format necessary for playing diverse media files and can perform encoding or decoding of media files by using a codec suitable for the format. The resource manager 1244 can manage resources such as a storage space, memory, or source code of at least one application of the application 1270.

The power manager 1245 can operate, for example, with a basic input/output system (BIOS) to manage a battery or power and can provide power information for an operation of an electronic device. The database manager 1246 can generate, search for, or modify database which is to be used in at least one application of the application 1270. The package manager 1247 can install or update an application which is distributed in the form of a package file.

The connectivity manager 1248 can manage, for example, wireless connection such as Wi-Fi or Bluetooth. The notification manager 1249 can display or notify an event such as arrival message, appointment, or proximity notification in a mode that does not disturb a user. The location manager 1250 can manage location information of an electronic device. The graphic manager 1251 can manage a graphic effect that is provided to a user or manage a user interface relevant thereto. The security manager 1252 can provide a general security function necessary for system security or user authentication. According to an embodiment, in the case where an electronic device (e.g., the electronic device 101) includes a telephony function, the middleware 1230 can further includes a telephony manager for managing a voice or video call function of the electronic device.

The middleware 1230 can include a middleware module that combines diverse functions of the above-described elements. The middleware 1230 can provide a module specialized to each OS kind to provide differentiated functions. Additionally, the middleware 1230 can remove a part of the preexisting elements, dynamically, or can add a new element thereto.

The API 1260 (e.g., the API 145) can be, for example, a set of programming functions and can be provided with a configuration which is variable depending on an OS. For example, in the case where an OS is the android or the iOS, it can be permissible to provide one API set per platform. In the case where an OS is the tizen, it can be permissible to provide two or more API sets per platform.

The application 1270 (e.g., the application program 147) can include, for example, one or more applications capable of providing functions for a home 1271, a dialer 1272, an SMS/MMS 1273, an instant message (IM) 1274, a browser 1275, a camera 1276, an alarm 1277, a contact 1278, a voice dial 1279, an e-mail 1280, a calendar 1281, a media player 1282, an album 1283, and a clock 1284, or for offering health care (e.g., measuring an exercise quantity or blood sugar) or environment information (e.g., atmospheric pressure, humidity, or temperature).

According to an embodiment, the application 1270 can include an application (hereinafter referred to as "information exchanging application" for descriptive convenience) to support information exchange between the electronic device (e.g., the electronic device 101) and an external electronic device (e.g., the electronic device 102 or 104). The information exchanging application can include, for example, a notification relay application for transmitting specific information to the external electronic device, or a device management application for managing the external electronic device.

For example, the notification relay application can include a function of transmitting notification information, which arise from other applications (e.g., applications for SMS/MMS, e-mail, health care, or environmental information), to an external electronic device (e.g., the electronic device 102 or 104). Additionally, the notification relay application can receive, for example, notification information from an external electronic device and provide the notification information to a user.

The device management application can manage (e.g., install, delete, or update), for example, at least one function (e.g., turn-on/turn-off of an external electronic device itself (or a part of components) or adjustment of brightness (or resolution) of a display) of an external electronic device (e.g., the electronic device 102) which communicates with the electronic device, an application running in the external electronic device, or a service (e.g., a call service, a message service, or the like) provided from the external electronic device.

According to an embodiment, the application 1270 can include an application (e.g., a health care application of a mobile medical device, and the like) which is assigned in accordance with an attribute of the external electronic device (e.g., the electronic device 102). According to an embodiment, the application 1270 can include an application which is received from an external electronic device (e.g., the electronic device 102). According to an embodiment, the application 1270 can include a preloaded application or a third party application which is downloadable from a server. The element titles of the program module 1210 according to the embodiment can be modifiable depending on kinds of OSs.

According to various embodiments, at least a part of the program module 1210 can be implemented by software, firmware, hardware, or a combination of two or more thereof. At least a portion of the program module 1210 can be implemented (e.g., executed), for example, by the processor (e.g., the processor 110). At least a portion of the program module 1210 can include, for example, a module, a program, a routine, sets of instructions, or a process for performing one or more functions.

The term "module" used in this disclosure can represent, for example, a unit including one or more combinations of hardware, software and firmware. For example, the term "module" can be interchangeably used with the terms "unit", "logic", "logical block", "component" and "circuit". The "module" can be a minimum unit of an integrated component or can be a part thereof. The "module" can be a minimum unit for performing one or more functions or a part thereof. The "module" can be implemented mechanically or electronically. For example, the "module" can include at least one of an application-specific IC (ASIC) chip, a field-programmable gate array (FPGA), and a programmable-logic device for performing some operations, which are known or will be developed.

At least a portion of an apparatus (e.g., modules or functions thereof) or a method (e.g., operations) according to various embodiments can be, for example, implemented by instructions stored in a computer-readable storage media in the form of a program module. The instruction, when executed by a processor (e.g., the processor 120), can cause the one or more processors to perform a function corresponding to the instruction. The computer-readable storage media, for example, can be the memory 130.

The computer-readable storage media according to various embodiments can store a program for executing an operation in which a communication module receives an application package from an external device and provides the application package to a normal module of a processor, an operation in which the normal module determines whether a secure application is included in at least a portion of the application package, and an operation in which the secure module of the processor installs the secure application in the secure module or in a memory associated with the secure module.

The computer-readable storage media can include a hard disk, a floppy disk, a magnetic media (e.g., a magnetic tape), an optical media (e.g., a compact disc read only memory (CD-ROM) and a digital versatile disc (DVD)), a magneto-optical media (e.g., a floptical disk), and hardware devices (e.g., a read only memory (ROM), a random access memory (RAM), or a flash memory). Also, a program instruction can include not only a mechanical code such as things generated by a compiler but also a high-level language code executable on a computer using an interpreter. The above-mentioned hardware devices can be configured to operate as one or more software modules to perform operations according to various embodiments, and vice versa.

Modules or program modules according to various embodiments can include at least one or more of the above-mentioned elements, some of the above-mentioned elements can be omitted, or other additional elements can be further included therein. Operations executed by modules, program modules, or other elements according to various embodiments can be executed by a successive method, a parallel method, a repeated method, or a heuristic method. Also, a part of operations can be executed in different sequences, omitted, or other operations can be added.

According to various embodiments of the present disclosure, a telemedicine service providing method may notify a user of the changed medical service policy, in the case where the user moves to an area and performs a medical service.

According to various embodiments of the present disclosure, the telemedicine service providing method can perform a telemedicine within a range of a medical service policy changed according to a guide provided by an electronic device.

According to various embodiments of the present disclosure, the telemedicine service providing method can reduce the inconvenience of deciding a medical service policy applied according to the movement of the user.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An electronic device comprising:
   a communication module configured to communicate with an external server for a telemedicine service;
   a sensor module;
   a processor; and
   a memory configured to store a first information about a premise for performing the telemedicine service in a first region and a second information about a premise for performing the telemedicine service in a second region,
   the memory further containing instructions that, when executed by the processor, cause the electronic device to:
   obtain a request for execution of an application that provides the telemedicine service,
   obtain location information of the electronic device by extracting a location to which a user is scheduled to move from schedule information comprising an image stored in memory,
   when the location information corresponds to the first region, display a first UI of the application, wherein the first UI corresponds to the first information,
   if the processor determines that the user is scheduled to move from the first region to the second region based on the schedule information, output a screen for notifying the second information or for receiving consent from the user,
   when the location information corresponds to the second region, display a second UI of the application, wherein the second UI corresponds to the second information,
   automatically perform a voice call function of the application with the external server if the processor determines that the first information or the second information satisfies a first condition, and automatically perform a video call function of the application with the external server if the first information or the second information satisfies a second condition.

2. The electronic device of claim 1, wherein the first UI and the second UI comprise at least one object for an authentication procedure, an authentication method, whether to check an item in a consent form, a telemedicine service method, or a combination thereof.

3. The electronic device of claim 1, wherein the memory further contains instructions, which when executed by the processor, cause the electronic device to receive at least one of the first information or the second information from an external electronic device by using the communication module.

4. The electronic device of claim 1, wherein the memory further contains instructions, which when executed by the processor, cause the electronic device to:
perform at least one function of the application if the first information or the second information satisfies a first condition; and
refrain from performing the at least one function if the first information or the second information satisfies a second condition.

5. The electronic device of claim 1, wherein the application comprises a first application and a second application, and
wherein the memory further contains instructions, which when executed by the processor, further cause the electronic device to:
automatically perform a function of the first application if the first information or the second information satisfies a first condition; and
automatically perform a function of the second application if the first information or the second information satisfies a second condition.

6. The electronic device of claim 1, wherein the memory further contains instructions, which when executed by the processor, cause the electronic device to receive the location information from another application.

7. A telemedicine service providing method that is performed by an electronic device, the method comprising:
storing a first information about a premise for performing the telemedicine service in a first region and a second information about a premise for performing the telemedicine service in a second region in a memory of the electronic device;
obtaining a request for execution of an application that provides the telemedicine service;
obtaining location information of the electronic device by extracting a location to which a user is scheduled to move from schedule information comprising an image stored in memory;
when the location information corresponds to the first region, displaying a first UI of the application, wherein the first UI corresponds to the first information;
if a processor of the electronic device determines that the user is scheduled to move from the first region to the second region based on the schedule information, outputting a screen for notifying the second information or for receiving consent from the user;
when the location information corresponds to the second region, displaying a second UI of the application, wherein the second UI corresponds to the second information;
automatically performing a voice call function of the application with an external server if the processor of the electronic device determines that the first information or the second information satisfies a first condition; and
automatically performing a video call function of the application with the external server if the first information or the second information satisfies a second condition.

8. The method of claim 7, wherein obtaining location information of the electronic device further comprises:
receiving at least one of the first information or the second information from an external electronic device by using a communication module included in the electronic device.

9. The method of claim 7, further comprising:
automatically performing a first set of functions of the application if the first information or the second information satisfies a first condition; and
automatically performing a second set of functions of the application if the first information or the second information satisfies a second condition.

* * * * *